US006232312B1

(12) United States Patent
Pamukcu et al.

(10) Patent No.: US 6,232,312 B1
(45) Date of Patent: May 15, 2001

(54) METHOD FOR TREATING PATIENT HAVING PRECANCEROUS LESIONS WITH A COMBINATION OF PYRIMIDOPYRIMIDINE DERIVATIVES AND ESTERS AND AMIDES OF SUBSTITUTED INDENYL ACETIC ACIDES

(75) Inventors: Rifat Pamukcu, Spring House, PA (US); Gary A. Piazza, Highlands Ranch, CO (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/027,334

(22) Filed: Feb. 20, 1998

Related U.S. Application Data

(63) Continuation of application No. 08/485,471, filed on Jun. 7, 1995, now abandoned.

(51) Int. Cl.[7] ..................... A61K 31/535; A61K 31/505; A61K 31/24; A61K 31/19

(52) U.S. Cl. ...................... 514/237.5; 514/258; 514/535; 514/537; 514/569

(58) Field of Search ................................. 514/258, 569, 514/535, 537, 237.5

(56) References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 4,950,680 | 8/1990 | Taylor et al. . |
| 5,073,559 | 12/1991 | Coates . |
| 5,147,875 | 9/1992 | Coates et al. . |
| 5,223,501 | 6/1993 | Chakravarty et al. . |
| 5,250,535 | 10/1993 | Verheyden et al. . |
| 5,254,571 | 10/1993 | Coates et al. . |
| 5,358,952 | 10/1994 | Moschel et al. . |
| 5,401,774 | 3/1995 | Pamukcu et al. . |
| 5,439,895 | 8/1995 | Lee et al. . |
| 5,614,530 | 3/1997 | Kumar et al. . |
| 5,614,627 | 3/1997 | Takase et al. . |
| 5,696,159 | 12/1997 | Gross et al. .................... 514/458 |

FOREIGN PATENT DOCUMENTS

| | | |
|---|---|---|
| 274218 | 12/1989 | (DD) . |
| 3038166 | 5/1981 | (DE) . |
| 0 347146 A2 | 12/1989 | (EP) . |
| 0 349 239 A2 | 1/1990 | (EP) . |
| 0 351058 | 1/1990 | (EP) . |
| 0 352960 A2 | 1/1990 | (EP) . |
| 0 395328 A2 | 10/1990 | (EP) . |
| 0 428268 A2 | 5/1991 | (EP) . |
| 0 463756 A1 | 1/1992 | (EP) . |
| 0 485157 A2 | 5/1992 | (EP) . |
| 0 485158 A2 | 5/1992 | (EP) . |
| 0 485171 A2 | 5/1992 | (EP) . |
| 0 485172 A2 | 5/1992 | (EP) . |
| 0 485173 A2 | 5/1992 | (EP) . |
| 0 508586 A1 | 10/1992 | (EP) . |
| 0 526004 A1 | 2/1993 | (EP) . |
| 0 607439 A1 | 7/1994 | (EP) . |
| 807826 | 1/1959 | (GB) . |
| 2063249 | 6/1981 | (GB) . |
| 56-53659 | 5/1981 | (JP) . |
| 57-167974 | 10/1982 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| 95-19978 | 7/1995 | (WO) . |
| WO 97/03985 | 2/1997 | (WO) . |

OTHER PUBLICATIONS

Waddell, W.R. et al. Am. J. Surgery, vol. 157, pp. 175–179 (1989).
Gonzaga, R.A.F. et al. The Lancet, Mar. 30, 1985, p. 751.
Waddell, W.R. et al. J. Surg. Oncology, vol. 24, pp. 83–87 (1983).
Federation Proceedings (1972) of the Federation of American Societies for Experimental Biology abstract Nos. 2044 and 2045.
Gilman, S.C. et al. Nonsteroidal Anti–inflammatory Drugs in Cancer Therapy, (circa 1985).
Brodgen, R.N et al. Drugs, vol. 16, pp. 97–114 (1978).

(List continued on next page.)

Primary Examiner—Jerome D. Goldberg
(74) Attorney, Agent, or Firm—Robert W. Stevenson

(57) ABSTRACT

Combinations of substituted indenyl acetic acids and pyrimido-pyrimidine derivatives are useful in the treatment of colonic polyps and inhibiting the growth of neoplastic cells.

14 Claims, No Drawings

OTHER PUBLICATIONS

Hucker, H.B. et al. Drug Metabolism & Disposition, vol. 1, No. 6, pp. 721–736 (1973).

Shen, T.Y. et al. Chemical and Biological Studies on Indomethacin, Sulindac and Their Analogs, pp. 107–178 (circa 1975).

Duggan, D.E. et al. Clin. Pharm. & Therapeutics, vol. 21, No. 3, pp. 326–335 (1976).

Duggan, D.E. et al. J. Pharm. & Exper. Therap., vol. 201, No. 1, pp. 8–13 (1977).

Glavin, G.B. et al. Toxicology and Applied Pharmacology, vol. 83, pp. 386–389 (1986).

Moorghen, M. et al. Journal of Pathology, vol. 156, pp. 341–347 (1988).

Moorghen, M. et al. Acta Histochemica, Suppl.–Band XXIX, S. 195–199 (1990).

Bjarnason et al. Gastroenterology, vol. 94, No. 4, pp. 1070–1074 (1988).

Badrieh, Y., et al. Chem. Ber., vol. 125, pp. 667–674 (1992).

Silvola, J. et al. Effects of nonsteroidal anti–inflammatory drugs on rat gastric mucosal phosphodiesterase activity, Agents and Actions, vol. 12.4, pp. 516–520 (1982).

Curtis–Prior, P.B. et al. Cyclic Nucleotide Phosphodiesterase Activity of Human Normal and Carcinomatous Lung Tissue, The Lancet, pp. 1225–1225 Dec. 4, 1976.

Pepin, P. et al. Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Lugnier, C. et al. Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al. Relaxation of guinea–pig trachae by cyclic AMP phosphodiesterse inhibitors and their enhancement by sodium mitroprusside, Br. J. Pharmacol. vol. III, pp. 1047–1052 (1994).

Weishaar, R.E. et al. Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al. Potential Use of Selective Phosphodiesterase Inhibitors in the Treatment of Asthma, New Drugs for Asthma Therapy, Birkhauser Verlag Basel, pp. 27–46 (1991).

Saeki, T. et al. Isolation of Cyclic Nucleotide Phosphodiesterase Isozymes From Pig Aorta, Biochem. Pharmacology, vol. 46, No. 5, pp. 833–839 (1993).

Turner, N.C. et al. Pulmonary effects of type V cyclic GMP specific phosphodiesterase inhibition in anaesthetized guinea–pig, Br. J. Pharmacol., vol. 111, 1198–1204 (1994).

Ferreira, S.H. et al. The molecular mechanism of action of peripheral morphine analgesia: stimulation of the cGMP system via nitric oxide release, European Journal of Pharmacology, 201 pp. 121–122 (1991).

Hidaka, H. et al. Selective Inhibitors of Three Forms of Cyclic Nucleotide Phosphodiesterase—Basic and Potential Clincial Applications, vol. 16, Advances in Cyclic Nucleotide and Protein Phosphorylation Research, pp. 245–259 (1984).

Tulshian, D. et al. Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al. Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073, 2081 (1992).

Broughton, B.J. et al. Antiallergic Activity of 2–Phenyl–8–azapruin–6–ones, Journal of Medicinal Chemistry, vol. 18, No. 11, pp. 1117–1118 (1975).

Kodama, K. et al. Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al. Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al. The Pyrimido–pyrimidine Derivatives RA 233 and RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al. Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al. Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al. 3',5'–Cyclic Nucleotide Phosphodiesterase in Tumor Cells as Potential Target for Tumor Growth Inhibition, Cancer Research 53, pp. 3058–3061 (1993).

Semmler, J. et al. Xanthine derivatives: comparison between suppression of tumor necrosis factor–x production and inhibition of cAMP phosphodiesterase activity, Immunology 78, pp. 520–525 (1993).

Mehta, Rajendra et al. Structure–Activity Relationships of Brassinin in Preventing the Development of Carcinogen–Induced Mammary Lesions in Organ Culture, Anticancer Research 14: 1209–1214 (1994).

Makaryan, A.P. et al. Cyclic Nucleotides in Patients with Malignant Neoplasms of the Colon, Laboratornoe Delo, vol. 8, pp. 31–33 (1991).

Carter et al. Chemotherapy of Cancer, $2^{nd}$ Ed., John Wiley & Sons, NY, NY, 1981, pp. 362–365.

Biddle, William et al. Antineoplastic Effect of the Pyrimido–Pyrimidine Derivative: RA 233, Pathologie Biologie, Jan., 1984, pp. 9–13.

Clarke, W.R. et al. The type III phosphodiesterase inhibitor milrinone and type V PDE inhibitor dipyridamole individually and synergistically reduce elevated pulmonary vascular resistance (Abstract Only), Pulm Pharmacol., 7(2), pp. 81–89, (1994).

Raeburn, David et al. Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al. Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnette, Mary S. et al. Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al. Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al. Characterization of 3':5'cyclic nucleotide phosphodiesterase activities of mouse neuroblastoma N18TG2 cells (Abstract Only), FEBS Lett. 324(1) pp. 76–80 (1993).

Porter, Roderick et al. Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al. Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al. Human Colorectal adenocarcinoma cells: differential nitric oxide synthesis determines their ability of aggregate platelets (Abstract Only), Cancer Res. 51(22) pp. 6073–6078 (1991).

Andersson, Tomas L. G. et al. Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Souness, John E. et al. Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al. Antimetastatic effect of flurbiprofen and other platelet aggregation inhibitors (Abstract Only), Neoplasma 33(4), pp. 417–421 (1986).

Hagiwara, Masatoshi et al. Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

D'Ancona, Silvia et al. Effect of dipyridamole, 5'–(N–ethyl)–carboxyamidoadenosine and 1,3–dipropyl–8–(2–amino–4–chlorophenyl)–xanthine on LOVO cell growth and morphology (Abstract Only), Anticancer Res. 14(1A) pp. 93–97 (1994).

Suzuki, Nobuo et al. Methods for the treatment of tumors with dipyridamole and interferons. (Abstract Only), U.S. Patent No. 5215744, 27 pages (1993).

Zhu, Enliang et al. Dipyridamole enhances 5–fluorouracil cytotoxicity in vitro. (Abstract Only), Shanghai Yixue 16(7), pp. 390–392 (1993).

Tzanakakis, George N. et al. Prevention of human pancreatic cancer cell–induced hepatic metastasis in nude mice by dipyridamole and its analog RA–233. (Abstract Only), Cancer (Philadelphia), 71(8), pp. 2466–2471 (1993).

Kuwabara, Hiroshi. Dipyridamole enhances cytotoxic effect of 1–β–D–arabinofuranosylcytosine on P388 murine leukemic cells. (Abstract Only), Mie Igaku, 36(1), pp. 129–135 (1992).

Ohnishi, Takanori et al. Potentiation of VP–16 cytotoxicity by dipyridamole in milignant [sic] glioma cells. (Abstract Only) Biol. Aspects Brain Tumors, Proc. Nikko Brain Tumor Conf. $8^{th}$, meeting date 1990, pp. 252–259 (1991).

Goel, Rakesh et al. Modulation of the activity of cancer chemotherapeutic agents by dipyridamole (Abstract Only), New Drugs, Concepts Results Cancer Chemother. pp. 19–44, 155–156 (1991).

Desai, Pankaj B. et al. Potentiation of cytotoxicity of mitoxantrone toward CHO–K1 cells in vitro by dipyridamole. (Abstract Only), Pharm. Res. 9(2), pp. 178–181 (1992).

Yung, Benjamin Yat Ming et al. Dipyridamole enhancement of doxorubicin–induced translocation of nucleophosmin and inhibition of cell growth in HL–60 cells. (Abstract Only), Int. J. Cancer 49(4), pp. 592–597 (1991).

Shalinsky, D.R. et al. Modulation of vinblastine sensitivity by dipyridamole in multidrug resistant fibrosarcoma cells lacking mdr1 expression. (Abstract Only), Br. J. Cancer 64(4), pp. 705–709 (1991).

Tatsuta, T. et al. Enhancement of activities of anti–tumor drugs by dipyridamole against multidrug–resistant human hepatoma PLC/PRF/5 cells. (Abstract Only), Anti–Cancer Drug. Des. 6(3), pp. 179–188, (1991).

Knight, Kenneth R. et al. Prostacyclin and prostanoid modifiers aid ischemic skin flap survival. (Abstract Only), J. Surg. Res. 50(2), pp. 119–123 (1991).

Mehta, Rajendra G. et al. Influence of thiols and inhibitors of prostaglandin biosynthesis on the carcinogen–induced development of mammary lesions in vitro. (Abstract Only) Anticancer Res. 11(2), pp. 587–591 (1991).

Sakaguchi, Yoshihisa et al. Combined treatment of adraimycin and dipyridamole inhibits lung metastasis of B16 melanoma cells in mice. (Abstract Only) Eur. Surg. Res. 22(4), pp. 213–218 (1990).

Chan, Thomas C. et al. Role of hypoxanthine and thymidine in determining methotrexate plus dipyridamole cytotoxicity. (Abstract Only), Eur. J. Cancer 26(8), pp. 907–911 (1990).

Kojima, Takayuki et al. Enhancement of an antitumor effect of interferon by dipyridamole in established human malignant melanoma cell lines. (Abstract Only), Int. J. Cancer 46(5), pp. 853–857 (1990).

Goel, Rakesh, et al. Pharmacologic basis for the use of dipyridamole to increase the selectivity of intraperitoneally delivered methotrexate. (Abstract Only), Cancer Chemother. Pharmacol. 25(3), pp. 167–172 (1989).

Shalinsky, David R. et al. Modulation of drug sensitivity by dipyridamole in multidrug resistant tumor cells in vitro. (Abstract Only), Cancer Res. 50(23), pp. 7537–7543 (1990).

Maehara, Yoshihiko et al. Potentiation of 5–fluorouracil cytotoxicity by combining hyperthermia and dipyridamole in vitro. (Abstract Only), Anticancer Res. 9(4), pp. 967–969 (1989).

Taguchi, Hirokuni et al. Growth–inhibitory effect of N–(phosphonoacetyl)–L–aspartic acid on human myeloid leukemia–derived cell lines and modulation by dipyridamole. (Abstract Only), Anticancer Res. 9(4), pp. 845–848 (1989).

Schwartz, Pauline M. et al. Dipyridamole potentiates the growth–inhibitory action of methotrexate and 5–flourouracil in human keratinocytes in vitro. (Abstract Only), J. Invest. Dermatol., 93(4), pp. 523–527 (1989).

Howell, Stephen B. et al. Dipyridamole enhancement of etoposide sensitivity. (Abstract Only), Cancer Res. 49(15), pp. 4147–4153 (1989).

Cao, Shousong et al. Potentiation of antimetabolite antitumor activity in vivo by dipyridamole and amphotericin B. (Abstract Only), Cancer Chemother. Pharmacol. 24(3), pp. 181–186 (1989).

Howell, Stephen B. et al. Comparison of the synergistic potentiation of etoposide, doxorubicin, and vinblastine cytotoxicity by dipyridamole. (Abstract Only), Cancer Res. 49(12), pp. 3178–3183 (1989).

Fischer, Paul H. et al. Enhancement of the sensitivity of human colon cancer cells to growth inhibition by acivicin achieved through inhibition of nucleic acid precursor salvage by dipyridamole. (Abstract Only), Cancer Res. 44(8), pp. 3355–3359 (1984).

Slichter, Sherrill J. et al. Interruption of tumor–associated platelet consumption with platelet enzyme inhibitors. (Abstract Only), Blood 59(6), pp. 1252–1258 (1982).

Barberi–Heyob, M. et al. Sequence–dependent growth–inhibitory effects of the in vitro combination of fluorouracil, cisplatin, and dipyridamole (Abstract Only), Cancer Chemother. Pharmacol. 33(2) pp. 163–170 (1993).

Jayaram, Hiremagalur N. et al. Schedule–dependent synergistic action of tiazofurin and dipyridamole on hepatoma 3924A cells (Abstract Only), Cancer Chemother. Pharmacol. 31(2) pp. 93–96 (1992).

Maehara, Yoshihko et al. Combined treatment of anticancer drugs with dipyridamole (Abstract Only), Igaku no Ayumi 164(5) pp. 273–276 (1993).

Zhen, Yongsu et al. Azidothymidine and dipyridamole as biochemical response modifiers: synergism with methotrexate and 5–fluorouracil in human colon an pancreatic carcinoma cells (Abstract Only), Oncol. Res. 4(2) pp. 73–78 (1992).

Suzuki, Nobuo et al. Dipyridamole enhances an antiproliferative effect of interferon in various types of human tumor cells (Abstract Only), Int. J. Cancer 51(4) pp. 627–633 (1992).

Jekunen, Antti et al. Synergism between dipyridamole and cisplatin in human ovarian carcinoma cells in vitro (Abstract Only), Cancer Res. 52(13) pp. 3566–3571 (1992).

Sakaguchi Yoshihisa et al. Dipyridamole augments the antitumor effects of fluorinated pyrimidines (Abstract Only), Anticancer Res. 12(1) pp. 119–121 (1992).

Maehara, Yoshihko et al. 5–Fluorouracil cytotoxicity is enhanced both in vitro and in vivo by concomitant treatment with hyperthermia and dipyridamole (Abstract Only), Cancer Chemother. Pharmacol. 29(4) pp. 257–260 (1992).

Kusumoto, Hiroki et al. Modulation of cytotoxic effect of anticancer drugs by dipyridamole in HeLa cells in vitro (Abstract Only), Anticancer Res. 10(6) pp. 1643–1645 (1990).

Busaid, Antonio et al, Effect of Dipyridamole on fluorodeoxyuridine cytotoxicity in vitro and in cancer patients (Abstract Only), Cancer Chemother. Pharmacol. 25(2) pp. 124–130 (1989).

El Hag, Imad Abdien et al, Potentiation by dipyridamole of 5–fluorouridine antitumor activity against a rat adenocarcinoma in vivo (Abstract Only), Anticancer Res. 10(1) pp. 29–32 (1990).

Scheithauer, W. et al. A study of various strategies to enhance the cytotoxic activity of 5–fluorouracil/leucovorin in human colorectal cancer cell lines (Abstract Only), Anticancer Res. 9(6) pp. 1793–1798 (1989).

Hirose, M. et al., Synergistic inhibitory effects of dipyridamole and vincristine on the growth of human leukemia and lymphoma cell lines (Abstract Only), Br. J. Cancer, 56(4), pp. 413–417 (1987).

Kennedy, D.G. et al. Enhancement of methotrexate cytotoxicity towards the MDA.MB.436 human breast cancer cell line by dipyridamole. The role of methotrexate polyglutamates (Abstract Only), Biochem. Pharmacol. 35(18) pp. 3053–3056 (1986).

Chan, Thomas C. K. et al. Mechanism of synergy between N–phosphonacetyl–L–aspartate and dipyridamole in a human ovarian carcinoma cell line (Abstract Only), Cancer Res. 45(8), pp. 3598–3604 (1985).

Chan, Thomas C. K. et al. Modulation of the activity of PALA by dipyridamole. (Abstract Only), Cancer Treat. Rep. 69(4), pp. 425–430 (1985).

Biddle, W. et al. Potentiation of the cell growth inhibitory effect of β–interferon by Mopidamole (Abstract Only), Proc. Soc. Exp. Biol. Med. 177(3) pp. 487–490 (1984).

Wolf, Lois M. et al. The in vitro interaction of RA–233 and several interferons on human cell lines (Abstract Only), J. Med. (Westbury, N.Y.) 15(1) pp. 15–21 (1984).

Bando, Hiroyasu et al. Role of platelets in cancer metastasis. Inhibitory effect of antiplatelet therapy on NK activity, and enhancing effect of PDGF [platelet derived growth factor] on tumor growth and metastasis (Abstract Only), Ketsueki to Myakkan 15(3) pp. 258–262 (1984).

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in APC$^{-/-}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncongene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

METHOD FOR TREATING PATIENT HAVING PRECANCEROUS LESIONS WITH A COMBINATION OF PYRIMIDOPYRIMIDINE DERIVATIVES AND ESTERS AND AMIDES OF SUBSTITUTED INDENYL ACETIC ACIDES

This application is a continuation of Ser. No. 08/485,471 filed Jun. 7, 1995, now abandoned.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps— literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

Recently, several non-steroidal anti-inflammatory drugs ("NSAIDs"), originally developed to treat arthritis, have shown effectiveness in inhibiting and eliminating polyps. Polyps virtually disappear when the patient take the drug, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for polyp treatment. Sulindac is a sulfoxide compound that itself is believed to be inactive an antiarthritic agent. The sulfoxide is reported to be converted by liver enzymes to the corresponding sulfide, which is acknowledged to be the active moiety as a prostaglandin inhibitor. The sulfide, however, is associated with the side effects of conventional NSAIDs. The sulfoxide is also known to be metabolized to a sulfone compound, which is regarded to be inactive as an inhibitor of prostaglandin synthesis.

SUMMARY OF THE INVENTION

This invention is a method of treating patients with precancerous lesions or neoplasms by administering a pharmacologically effective amount of a combination of compound of Formula I and compound of Formula II below to a patient in need of such treatment. Such compositions are effective in modulating apoptosis, and eliminating and inhibiting precancerous lesions, and neoplastic cells.

It was unexpectedly discovered that the combination of these compounds achieved surprising results inducing apoptosis in neoplastic cells. Therefore, this combination may be useful for treating patients with precancerous lesions.

DETAILED DESCRIPTION OF THE PRESENTLY PREFERRED EMBODIMENTS

As discussed above, this invention is a method of treating a patient with precancerous lesions or neoplasms by administering a pharmacologically effective amount of a combination of the compound represented by the following Formula (I) and the compound represented by the following Formula (II), or the pharmacologically acceptable salts thereof;

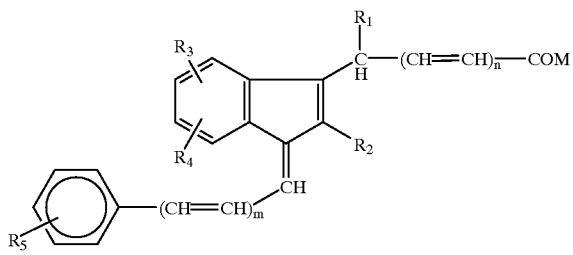

(I)

wherein $R_1$ is selected from the group consisting of hydrogen, lower alkyl, or haloalkyl;

$R_2$ is selected from the group consisting of hydrogen or alkyl;

$R_3$ and $R_4$ are one or more members each independently chosen from the group consisting of hydrogen, alkyl, acyloxy, alkoxy, nitro, amino, acylamino, alkylamino, diakylamino, dialkylaminoalkyl, sulfamyl, alkythio, mercapto, hydroxy, hydroxyalkyl, alkylsulfonyl, halogen, cyano, carboxyl, carbalkoxy, carbamido, haloalkyl, or cycloalkoxy;

$R_5$ is alkylsulfonyl;

m is 0 or 1;

n is 0 or 1; and

M is selected from the group consisting of hydroxy, substituted lower alkoxy, amine, alkylamino, dialkylamino, N-morpholino, hydroxyalkylamino, polyhydroxyamino, dialkylaminoalkylamino, aminoalkylamino, and the group OMe, wherein Me is a cation.

Preferably, the aforesaid method involves the administration of compounds of formula I wherein m and n are zero.

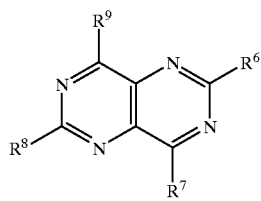

(II)

wherein from two to four, inclusive, of the substituents $R_6$, $R_7$, $R_8$ and $R_9$ are basic moieties selected from the group consisting of amino, lower alkylamino, dialkylamino wherein the alkyl moieties have from 1 to 12 carbon atoms, mono-(hydroxy-lower alkyl)-amino, di-(hydroxy-lower alkyl)-amino, (hydroxy-lower alkyl)-alkyl-amino wherein the alkyl moiety has from 1 to 12 carbon atoms, (lower alkoxy-lower alkyl)-amino, lower alkenyl-amino, cyclohexyl-amino, phenyl-amino, halophenyl-amino, nitrophenyl-amino, (lower alkoxy-phenyl)-amino, [(di-lower alkyl-amino)-phenyl]-amino, benzylamino, semicarbazidyl, hydrazinyl, guanidyl, ethyleneimino, piperidyl, lower alkyl-piperidyl, lower alkoxy-piperidyl, hydroxy-piperidyl, pyrrolidyl, lower alkyl-pyrrolidyl, lower alkoxy-pyrrolidyl, hydroxy-pyrrolidyl, morpholyl, lower alkyl-morpholyl, lower alkoxy-morpholyl, hydroxy-morpholyl, tetrahydropyridyl, lower alkyl-tetrahydropyridyl, lower alkoxy-tetrahydropyridyl, hydroxy-tetrahydropyridyl, hexamethyleneimino, lower alkyl-hexamethyleneimino, lower alkoxy-hexamethyleneimino, hydroxy-hexamethyleneimino, tetrahydroquinolyl, lower alkyl-tetrahydroquinolyl, lower alkoxy-tetrahydroquinolyl, hydroxy-tetrahydroquinolyl, piperazyl, lower alkylpiperazyl, lower alkoxy-piperazyl, hydroxy-piperazyl and N'-lower alkyl-piperazyl, and the remaining substituents $R_6$ to $R_9$ are selected from the group consisting of hydrogen, halogen, hydroxyl, mercapto, lower alkyl, phenyl, lower alkoxy, di-lower-alkyl-amino-lower alkoxy and lower alkyl-thio, phenyl-thio, benzyl-thio, lower alkoxy-lower alkoxy, their non-toxic alkali metal salts and their non-toxic acid addition salts.

Preferably, $R_6$ and $R_8$ are independently selected from the group consisting of amino, lower alkylamino, dialkylamino, mono-(hydroxy-lower alkyl)-amino, di-(hydroxy-lower alkyl)-amino and (hydroxy-lower alkyl)-alkyl-amino. More preferably $R_6$ and $R_8$ are diethanolamino.

Preferably, $R_7$ and $R_9$ are independently selected from the group consisting of hydrogen, halogen, piperidyl, substituted piperidyl, pyrrolidyl, substituted pyrrolidyl, morpholyl and substituted morpholyl. More preferably, either $R_7$ or $R_9$, or both, are piperidyl.

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer. and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

It was unexpectedly discovered that the combination of compound of Formula I and compound of Formula II achieved surprising results in inducing apoptosis in neoplastic cells.

Compounds of Formula I and Formula II may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I and Formula II, excipients such as cocoa butter or a suppository wax.

The pharmaceutically acceptable carrier and compounds of Formula I and Formula II are formulated into unit dosage forms for administration to a patient. The dosage levels of active ingredient (i.e. compounds of Formula I and II) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of regulating apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of a combination of the compound of formulae [I] and [II] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formulae above.

Preferable specific examples of the compound will now be described in order to facilitate the understanding of the present invention, though it is needless to say that the compounds of the present invention are not limited to these examples.

The following Examples 1–19 are of compounds of Formula I.

EXAMPLE 1

5-Methoxy-2-Methyl-1-(ρ-Methylsulfinylbenzylidene)-3-Indenyl Acetic Acid (A) α-Methyl-β-(ρ-methylthiophenyl) propionic acid To a solution of 2.3 g. (0.1 mole) of sodium in 100 ml. of absolute alcohol is added 17.4 g. (0.1 mole) of diethyl methylmalonate and 17.3 g. (0.1 mole) of ρ-methylthiobenzylchloride. The mixture is heated under a reflux in a water bath for three hours. The reaction mixture is poured into water, and the aqueous solution is extracted six times with ether and dried. It is then evaporated to yield diethyl methyl-ρ-methylthiobenzyl malonate. The crude product is then saponified by heating with excess 4% sodium hydroxide in aqueous ethanolic solution. The solution thus formed is concentrated, extracted with ether to remove any neutral material, and acidified with dilute sulfuric acid. The acidic mixture is heated on a steam bath for one hour, cooled and then extracted with ether. Evaporation of the ether solution gives α-methyl-β-(ρ-methylthiophenyl) propionic acid.

In a similar manner, using other substituted malonic esters in place of diethyl methylmalonate and other substituted benzyl halides in place of ρ-methyl-thiobenzyol chloride, the corresponding substituted propionic acids are obtained, for example:

α-methyl-β-(ρ-methoxyphenyl)propionic acid,
α-allyl-β-(ρ-nitrophenyl)propionic acid.

(B) 6-methoxy-2-methylindanone

α-Methyl-β-(ρ-methoxyphenyl)propionic acid (15 g.) is added to polyphosphoric acid (170 g.) at 50° C. and the mixture is heated at 83–90° for two hours. The syrup is poured into iced water, stirred for one-half hour, and then extracted with ether three times. The ether solution is washed with water twice, and with 5% $NaHCO_3$ five times until all the acidic material has been removed. The remaining neutral solution is washed with water and dried over sodium sulfate. Evaporation of the solution gives the indanone as a pale yellow oil.

In a similar manner, other β-aryl propionic acid compounds are converted to the corresponding indanone by the procedure of this example.

(C) Methyl 5-methoxy-2-methyl-3-indenylacetate.

A solution of 13.4 g. of 6-methoxy-2-methyl-indanone and 19.3 g. of methyl bromoacetate in 45 ml. benzene is added over a period of 5 minutes to 21 g. of zinc amalgam (prepared according to Org. Syn. Coll., vol. 3) in 110 ml. benzene and 40 ml. dry ether. A few crystals of iodine are added to start the reaction, and the reaction mixture is maintained at reflux temperature (ca. 65°) with external heating. At 3 hour intervals, two batches of 10 g. zinc amalgam and 10 g. bromoester are added, and the mixture is then refluxed for 8 hours. After addition of 30 ml. ethanol and 150 ml. of acetic acid, the mixture is poured into 700 ml. of 1:1 aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temp.) (1–2 mm.) gives crude methyl(1-hydroxy-2-methyl-methoxy-indenyl)acetate.

A mixture of the above crude hydroxyester, 20 g. of ρ-toluenesulfonic acid monohydrate and 20 g. of anhydrous calcium chloride in 250 ml. toluene is refluxed overnight. The solution is filtered, and the solid residue is washed with benzene. The combined benzene solution is washed with water, sodium bicarbonate, water and then dried over sodium sulfate. After evaporation, the crude methyl 5-methoxy-2-methyl-3-indenylacetate is chromatographed on acid-washed alumina, and the product is eluted with petroleum ether-ether (v./v. 50–100%).

METHYL 2,6-DIMETHYL-3-INDENYLACETATE

The above reactions of Example 1C are repeated except that the starting materials are 2,5-dimethylindanone and methylbromoacetate. Using the same reaction conditions and techniques there is obtained methyl 2,6-dimethyl-3-indenylacetate.

The above reactions of Example 1C are repeated except that the starting materials are 6-methylthiolindanone and methylbromoacetate. Using the same reaction conditions and techniques, there is obtained methyl 5-methyl-thio-2-methyl-3-indenyl-acetate.

When any of the other indanones described in the other examples of the specification are used in the above procedure in place of 6-methoxy-2-methylindanone the corresponding methyl ester is obtained.

(D) 5-methoxy-2-methyl-1-(ρ-methylthio-benzylidene)-3-indenyl acetic acid

To a solution of methyl 5-methoxy-2-methyl-3-indenylacetate 8.7 g. (0.037 mole) and ρ-methyl-thiobenzaldehyde, 6.3 g. (1.1 equivalent) is added 16+ ml. (2.0+ equivalents) of 25% methanolic sodium methoxide. The mixture is stirred at reflux under nitrogen for 2 hours. An equal volume of water is added dropwise and refluxing continues for 30 min. The solution is cooled, diluted with water and extracted with ether (3×). Residual ether is blown off with nitrogen, and then the aqueous solution is acidified with 50% glacial acetic acid. The precipitated product is collected and washed thoroughly with water. The crude product is crystallized from methanol to give pure 5-methoxy-2-methyl-1-(ρ-methylthiobenzylidene)-3-indenyl acetic acid (M.P. 195–196°).

5-NETHOXY-2-METHYL-1-(P-ETHYLTHIOBENZYLIDENE)-3-INDENYL ACETIC ACID

The above reaction of Example 1D is repeated using ρ-ethylthiobenzaldehyde instead of ρ-methyl-thiobenzaldehyde. Using the same reaction conditions and techniques, there is obtained 5-methoxy-2-methyl-1-(ρ-ethylthiobenzylidene)-3-indenyl acetic acid.

5-HYDROXY-2-METHYL-1-(βMETHYLTHIOBENZYLIDENE-3-INDENYL ACETIC ACID

The reaction of Example 1D is repeated except that the starting materials are methyl 5-hydroxy-2-methyl-3- indenylacetate and ρ-methylthiobenzaldehyde. Using the same reaction conditions and techniques, there is obtained 5-hydroxy-2-methyl-1-(ρ-methyl-thiobenzylidene)-3-indenyl acetic acid.

The other methyl esters of Example 1C are reacted with ρ-methylthiobenzaldehyde according to the above procedure to produce the corresponding indenyl acetic acid.

(E) 5-methoxy-2-methyl-1-(ρ-methylsulfinylbenzyl-idene)-3-indenyl acetic acid

A solution of sodium periodate (0.214 g.; 0.001 mole) in 3 ml. of water is added dropwise to 5-methoxy-2-methyl-1-(ρ-methylthiobenzylidene)-3-indenyl acetic acid (0.352 g.) (0.001 mole) in 25 ml. methanol and enough acetone to cause solution. This solution is stirred overnight at room temperature and filtered. The filtrate is evaporated at 30° to a sufficiently small volume that causes the product to precipitate. The suspension is diluted with several volumes of water, cooled and collected. The product is dried in vacuo over potassium hydroxide pellets and then in a vacuum oven at 70° to give 5-methoxy-2-methyl-1-(ρ-methylsulfinylbenzylidene)-3-indenyl acetic acid (M.P. 200.5–203.5°).

5-methoxy-2-methyl-1-(ρ-methylsulfonyl-benzylidene)-3-indenyl acetic acid is prepared by the addition of 1.0 mole of m-chloroperbenzoic acid per mole of 5-methoxy-methyl-1-(ρ-methylsulfinylbenzyl-idene)-3-indenyl acetic acid in an acetone solution. ($R_1$=hydrogen; $R_2$=$CH_3$; $R_3$=5—$OCH_3$; $R_4$=hydrogen; $R_5$=p—$CH_3SO$)

Similarly, poly-5-methoxy-2-methyl-1-(ρ-ethylsulfinylbenzylidene)-3-indenyl acetic acid and poly-5-hydroxy-2-methyl-1-(ρ-methylsulfinylbenzyl-idene)-3-indenyl acetic acid be produced following the reaction of Example 1E using the compounds from Example 1D.

EXAMPLE 2

5-Methoxy-2-Methyl-1-(ρ-Methvlsulfinylbenzylidene)-3-Indenyl Acetic Acid (A) 6-methoxy-2-methylindanone In a 500 ml. 3-necked flask is placed 36.2 g. (0.55 mole) of zinc dust, and in a 250 ml. addition funnel is charged a solution of 80 ml. anhydrous benzene, 20 ml. of anhydrous ether, 80 g. (0.58 mole) of ρ-anisaldehyde and 98 g. (0.55 mole) of ethyl-2-bromopropionate. About 10 ml. of the solution is added to the zinc dust with vigorous stirring, and the mixture is warmed gently until an exothermic reaction commences. The remaining reactants are added dropwise at such a rate that the reaction mixture is refluxing smoothly on its own accord (ca. 30–35 min.). After addition is completed, the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid, and washed twice with 50 ml. portions of 5% sulfuric acid and washed twice with 50 ml. portions of water. The aqueous acidic layers are combined and extracted with 2×50 ml. ether. The combined etherel and benzene extracts are dried over sodium sulfate. Evaporation of solvent and fractionation of the residue through a 6" Vigreux column affords the product, ethyl-2-hydroxy-(ρ-methoxyphenyl)-1-methylpropionate, B.P. 155–160° (1.5 mm).

By the method described in Vanden Zanden, Rec. trav. chim., 68, 413 (1949), the above compound is converted to 6-methoxy-2-methylindanone.

5-ETHYL-2-METHYLINDANONE

The above reactions of Example 2A are repeated except that the starting materials are o-ethylbenzaldehyde and ethyl-2-bromopropionate. Using the same reaction conditions and techniques, there is obtained 5-ethyl-2-methylindanone.

When the benzaldehydes listed in Table I below are utilized in the procedure of Example 2A, the corresponding indanone is obtained.

TABLE I

| Aldehyde | Indanone |
| --- | --- |
| ρ-o-, or m-tolualdehyde | 2, 6-dimethyl, 2, 5-dimethyl, or 2, 4-dimethyl-indanone |
| ρ-o-, or m-hydroxybenzaldehyde | 4, 5 or 6-hydroxy-2-methylindanone |
| ρ-o-, or nitrobenzaldhyde | 2-methyl-(4, 5 or 6) nitroindanone |
| ρ-o-, or m-chlorobenzaldehyde | (4, 5, or 6) chloro-2-methylindanone |
| ρ-o-, or m-cyanobenzaldehyde | (4, 5, or 6) cyano-2 methylindanone |
| Vanillin | 6-hydroxy-5-methoxy 2-methylindanone |
| ρ-o-, or m-sulfamylbenzaldehyde | 2-methyl-(4,5 or 6-sulfamylindanone |
| 3-chloro-4-methylbenzaldehyde | 5-chloro-2,6 dimethylindanone |
| 4-carbamide-5-methylbenaldehyde | 6-carbomide-2,5 dimethylindanone |
| 3,4-difluorobenzaldhyde | 5, 6 difluoro-2-methylindanone |

(B) 5-methoxy-2-methyl-1-(ρ-methylsulfinylbenzylidene)-3-indenyl acetic acid

The reactions of Examples 1C, 1D and 1E are repeated, and 5-methoxy-2-methyl-1-(ρ-methylsulfinyl-benzylidene)-3-indenyl acetic acid is obtained. ($R_1$=hydrogen; $R_2$=$CH_3$; $R_3$=5—O—$CH_3$; $R_4$=hydrogen; $R_5$=ρ—$CH_3SO$)

EXAMPLE 3

1-(ρmethylsulfonylbenzylidene-2-Methyl-5-Methoxy-3-Indenyl)-Propionic Acid (A) Methyl-α (5-methoxy-2-methyl-3-indenyl) propionate The procedure of Example 1C is followed using methyl α-bromopropionate in equivalent quantities in place of methyl bromoacetate used therein. There is obtained methyl α-(1-hydroxy-6-methoxy-2-methyl-1-indenyl)propionate, and it is then dehydrated to methyl α-(5-methoxy-2-methyl-3-indenyl)propionate in the same manner.

(B) α-[1-(ρ-methylthiobenzylidene)-2-methyl-5-methoxy-3-indenyl] propionic acid

To a solution of 0.5 g. (0.00192 mole) of methyl α-(5-methoxy-2-methyl-3-indenyl) propionate and 0.595 g. (0.0039 mole) of ρ-methylthiobenzaldehyde in 3 ml. of anhydrous pyridine is added 1.63 g. of a 40% solution of benzyltrimethylammonium hydroxide (Triton-B) in methanol. The resulting red-purple solution is stirred at room temperature overnight.

The reaction mixture is poured into a mixture of ice and water, acidified with 2.5 N HCl, and extracted with ether. The ether solution is then washed with 2.5 N HCl until the washing acidifies (once), then with water until neutral. The ether layer is then extracted with 5% $Na_2CO_3$ solution. The $Na_2CO_3$ solution is washed with ether, acidified and extracted with ether. The ether solution is washed with water, dried over Na$_2$SO$_4$ and concentrated in vacuo to a yellow oil that foams up to a clear yellow solid on pumping at 0.5–1 mm. Thin layer chromatography of the product shows only one spot when eluted with a (v./v. 4:3:5) of isopropanol: 10% NH$_4$OH: ethyl acetate mixture;

U.V. absorption: >max, 3525, 2910, 2540, 2450. E %, 399, 260, 510 and 498.

(C) α-[1-(ρ-methylsulfinylbenzylidene)-2-methyl 5-methoxy-3-indenyl]-propionic acid The procedure of Example 1E is followed using α-[1-(ρ-methylthiobenzylidene)-2-methyl-5-methoxy-3-indenyl]-propionic acid in place of 5-methoxy-2-methyl-1-(ρ-methylthiobenzylidene)-3-indenyl acetic acid thereby producing α-[1-(ρ-methylsulfinylbenzylidene)-2-methyl-5-methoxy-3-indenyl]-propionic acid (M.P. 115–120°).

α-[1-(ρ-methylsulfonylbenzylidene-2-methyl-5-methoxy-3-indenyl]-propionic acid is produced by the addition of 1.0 mole of m-chloroperbenzoic acid per mole of α[1-(ρ-methylsulfinylbenzylidene)-2-methyl-5-methoxy-3-indenyl]-propionic acid as described in Example 1E. ($R_1$=CH$_3$; $R_2$=CH$_3$; $R_3$=5-methoxy; $R_4$=hydrogen; $R_5$=CH$_3$SO$_2$—)

EXAMPLE 4

1-ρ-Methylsulfonylbenzylidene-5-Dimethylamino-3-Indenyl Acetic Acid (A) Methyl-3-hydroxy-2-methyl-5-nitro-3-indenylacetate The procedure of Example 1C is followed using 2-methyl-6-nitro indanone in equivalent quantities in place of 6-methyoxy-2-methyl-indanone used therein. After the mixture is condensed, 30 ml. of ethanol and 50 ml. of acetic acid are added. The mixture is then poured into 700 ml. of water. Extraction with ether gives methyl 3-hydroxy-2-methyl-5-nitro-3-indenyl-acetate.

(B) Methyl 5-dimethylamino-2-methyl-3-indenylacetate

A solution of 0.05 mole of methyl 3-hydroxy-2-methyl-5-nitro-3-indenylacetate, 0.2 mole of 38% aqueous formaldehyde and 2 ml. of acetic acid in 100 ml. ethanol is reduced catalytically in the presence of a 10% Pd/C catalyst under 40 lb. p.s.i. hydrogen pressure at room temperature. The solution is filtered, evaporated and chromatographed on 300 g. of silica gel to give methyl 5-dimethylamino-3-hydroxy-2-methyl-3-indenylacetate. The hydroxy ester is then dehydrated to methyl 5-dimethylamino-2-methyl-3-indenylacetate.

(C) 1-ρ-methylthiobenzylidene-5-dimethylamino-2-methyl-3-indenyl acetic acid

To a solution of 2.5 g. of the ester from Part B of this example in 15 ml. of 1,2-dimethoxyethane at 0° is added 1.5 g. of ρ-methylthiobenzaldehyde followed by 1.1 g. of potassium t-butoxide. The reaction mixture is kept in the ice-bath for 4 hours, and then allowed to stand at room temperature for 18 hours. The mixture is diluted with 15 ml. of ether and the potassium salt is filtered. The salt is dissolved in 30 ml. of water and neutralized with dilute hydrochloric acid to pH 6–6.5. The crude acid precipitated is collected by filtration and chromatographed on a silica gel column, using ether-petroleum ether (v./v. 50–100t) as eluent to give pure 1-ρ-methylthiobenzylidene-5-dimethylamino-2-methyl-3-indenyl acetic acid which may be oxidized to 1-ρ-methylsulfinylbenzylidene- 5-dimethylamino-2-methyl-3-indenyl acetic acid and 1-ρ-methylsulfonylbenzylidene-5-dimethylamino-2-methyl-3-indenyl acetic acid as described above. ($R_1$=hydrogen; $R_2$=CH$_3$; $R_3$=5—N(CH$_3$)$_2$; $R_4$=hydrogen; $R_5$=CH$_3$SO$_2$—)

EXAMPLE 5

(1-ρ-Methylsulfinylbenzylidene)-2-Methyl-5-Dimethylamino-3-Indenyl-Propionic Acid (A) α-[1-(ρ-methylsulfinylbenzylidene)-2-methyl-5-dimethylamino-3-indenyl]-propionic acid The procedure of Examples 2A, B and C is followed using 6-dimethylamino-2-methylindanone in place of 6-methoxy-2-methylindanone and methyl-α-bromopropionate in place of methyl bromoacetate used therein. There is obtained α-[1-(ρ-methylsulfinyl-benzylidene)-2-methyl-5-dimethylamino-3-indenyl]-propionic acid. ($R_1$=CH$_3$; $R_2$=CH$_3$; $R_3$=5-dimethylamino; $R_4$=hydrogen; $R_5$=p—CH$_3$SO—)

EXAMPLE 6

5,6-Difluoro-2-Methyl-1-(ρ-Methylsulfinyl-benzylidene)-3-Indenyl Acetic Acid (A) 3,4-difluorobenzaldehyde In a 250 ml. three-necked flask equipped with a magnetic stirrer, thermometer, condenser, and dropping funnel is placed 25.6 g (0.2 mole) of 3,4 difluorotoluene. The liquid is heated to 105° and illuminated as 67 g. (0.42 mole) of bromine is added slowly. The temperature is kept between 105–110° while the first half of the bromine is added over a period of one hour. The rest of the bromine is added over approximately a 2-hour period and the temperature is raised to 150° and kept there for 5 minutes.

The reaction mixture is cooled and transferred to a 1 liter 3-necked flask with a motor driven stirrer and condenser. 120 ml. H$_2$O and 90 g. of calcium carbonate are added, and the mixture is refluxed for 20 hours with good stirring. The reaction mixture is steam distilled until no further oil is collected. The oil is taken up in methylene chloride and dried over MgSO$_4$. Evaporation of the solvent yields 3,4-difluorobenzaldehyde which is used without further purification.

(B) 3,4-difluoro-α-methylcinnamic acid

A mixture of 2.88 g. (0.02 mole) of 3,4-difluorobenzaldehyde, 3.24 g. (0.025 mole) of propionic anhydride and 0.92 g. (0.02 mole) of sodium propionate under nitrogen is heated at 135° with a magnetic stirrer for 20 hours. The reaction mixture is poured onto 50 ml. of water. A solid precipitates that dissolves when 50 ml. of saturated K$_2$CO$_3$ is added with stirring. The basic solution is extracted with ether (2×100 ml.). The aqueous phase is then poured into an excess of concentrated HCl and ice. The precipitated white solid is filtered and dried to give 3,4-difluoro-α-methylcinnamic acid, M.P. 122–125°.

4-TRIFLUOROMETHYL-α-METHYLCINNAMIC ACID

The above reaction of Example 6A is repeated except that 4-trifluoromethylbenzaldehyde is used as a starting material in place of 3,4-difluorobenzaldehyde. Using the same reaction conditions and techniques there is obtained 4-trifluoromethyl-α-methylcinnamic acid.

Similarly using other benzaldehydes such as 4-methylthiobenzaldehyde, 4-chlorobenzaldehyde, and 3-methyl-4-chlorobenzaldehyde, there is obtained 4-methylthio-α-methylcinnamic acid, 4-chloro-α-methylcinnamic acid and 3-methyl-4-chloro-α-methylcinnamic acid respectively.

(C) 3,4-difluoro-α-methylhydrocinnamic acid 28 g. (0.141 mole) of 3,4-difluoro-α-methyl-cinnamic acid, 1 g. of PtO$_2$ in 250 ml. of MeOH is hydrogenated at 45 p.s.i. until the theoretical uptake is completed. The catalyst is filtered off, and the material evaporated to one-third its volume. A 15% potassium hydroxide solution (10 ml.) is added, and the mixture refluxed for 30 minutes when it is poured into water and extracted with ether (2×100 ml.). The aqueous layer is acidified with concentrated HCl and ice.

The oil which comes out is extracted into ether, the ether solution dried over MgSO$_4$ and evaporated to leave a clear oil which crystallizes. 3,4-difluoro-α-methylhydrocinnamic acid, M.P. 55–56°, is isolated.

(D) 5,6-difluoro-2-methyl-1-indanone 20 g. (0.1 mole) of 3,4-difluoro-α-methyl-hydrocinnamic acid is added to 250 g. of polyphosphoric acid. The mixture is efficiently stirred and heated on a steam bath for 2 hours. The mixture is poured onto ice-water (400 ml.). The precipitate is extracted with ether (3×100 ml.). The extract is washed with saturated potassium carbonate, water and then dried (MgSO$_4$). The ether solution, when evaporated, leaves solid 5,6-difluoro-2-methyl-1-indanone (M.P. 66–68°) which is used without further purification.

(E) 5,6-difluoro-2-methylindene-3-acetic acid methyl ester

A mixture of 9.1 g. (0.05 mole) of 5,6-difluoro-2-methyl-1-indanone, 4.0 g. of "activated" zinc dust, 7.6 g. (0.05 mole) of methyl bromoacetate, and a crystal of iodine in 250 ml. of dry benzene is refluxed for 4–5 hours. Tlc (20% Et$_2$O-80% pet. ether on Si gel) shows greater than 95% conversion at this time. The reaction mixture is poured onto 250 ml. of 5% H$_2$SO$_4$, separated, and dried (MgSO$_4$). Removal of solvent leaves an oily hydroxy ester. The crude ester is redissolved in 100 ml. of benzene and phosphorus pentoxide (20 g.) is added. The mixture is refluxed for 30 minutes (no stirrer necessary) and decanted. The residue is washed with benzene, the organic layers combined, washed with water (2×100 ml.) and dried (MgSO$_4$). The benzene, when evaporated, leaves 5,6-difluoro-2-methylindene-3-acetic acid methyl ester, M.P. 86–90°.

5-METHYLTHIO-2-METHYLINDENE-3-ACETIC ACID METHYL ESTER

The above reaction of Example 6E is repeated using 5-methylthio-2-methylindanone instead of 5,6-difluoro-2-methyl-1-indanone. Using the same conditions and techniques, there is obtained 5-methylthio-2-methylindene-3-acetic acid methyl ester.

When an acylamino or sulfonyl indanone is employed as the starting material in the above procedure, the corresponding methyl ester is obtained.

(F) 5,6-difluoro-2-methyl-1-(ρ-methylthio-benzylidene)-indene-3-acetic acid 1.19 g. (5.0 mole) of 5,6-difluoro-2-methyl-indene-3-acetic acid methyl ester is dissolved in 10 ml. of dry pyridine followed by 0.76 g. (5.0 mole) of ρ-methylthiobenzaldehyde. The flask is placed under nitrogen, and 5.0 g. (5.1 mole) of Triton B is added. The deeply colored solution is allowed to stand overnight, and then water (2 ml.) is added. After standing for 15 minutes, it is poured into an excess of water. The organics are extracted with ether (2×50 ml.). The aqueous phase is added to 10% HCl-ice. The orange, gummy solid that precipitates is extracted into methylene chloride and dried (MgSO$_4$). The solvent is removed to leave an orange solid. The solid is filtered to give a crude product which is recrystallized from benzene to give 5,6-difluoro-2-methyl-1-(ρ-methylthiobenzylidene)-indene-3-acetic acid. M.P. 181–182.5°. When 3-methylthio-2-furaldehyde or 2-methylthio-5-pyrazine aldehyde is utilized in the above procedure instead of ρ-methylthiobenzaldehyde the corresponding indene acetic acid is obtained.

(G) 5,6-difluoro-2-methyl-1-(ρ-methylsulfinyl-benzylidene)-indene-3-acetic acid

To a solution of 0.358 g. (1.0 mole) of 5,6-difluoro-2-methyl-1-(ρ-methylthiobenzylidene)-indene-3-acetic acid in acetone (10 ml.) is added 10–15 ml. MeOH. With magnetic stirring, 0.32 g. (1.5 mole) of sodium meta periodate is added in 5 ml. of water. The proportions of acetone, methanol and water are adjusted if necessary to preserve homogeneity. After several minutes, a precipitation of sodium iodate appears. The suspension is stirred at room temperature for 16 hours, and then poured into approximately 50 ml. of water and 100 ml. methylene chloride. The two phases are separated and the water layer is extracted twice with methylene chloride. The organic phases are washed with water and dried (MgSO$_4$). The residue after evaporation is dissolved in the minimum amount of boiling ethyl acetate and allowed to stand for 12 hours in the freezer compartment. The deep orange crystals are filtered. The filtrate is reduced to ½ volume and allowed to stand in the cold for several hours to give a large second crop. In this way, 5,6-difluoro-2-methyl-1-(ρ-methylsulfinylbenzylidene)-3-indenylacetic acid is isolated, M.P. 200–210°. (R$_1$=hydrogen; R$_2$=CH$_3$; R$_3$=5-fluoro; R$_4$=6-fluoro; R$_5$=CH$_3$—SO—).

EXAMPLE 7

5,6-Difluoro-2-Methyl-1-(ρ-Methylsulfonyl-benzylidene)-Indenyl-3-Acetic Acid (A) 5-6,difluoro-2-methyl-1-(ρ-methyl-sulfonylbenzylidene)-indene-3-acetic acid To 5-6,difluoro-2-methyl-1-(ρ-methylsulfinyl-benzylidene)-indene-3-acetic acid (0.005 mole) in acetone (15 ml.) is added, slowly with stirring, m-chloroperbenzoic acid (0.005 mole). The mixture is heated and evaporated to near dryness at 40°. The solid is washed with boiling water (4×50 ml.) and dried yielding 5,6-difluoro-2-methyl-1-(ρ-methyl-sulfonylbenzylidene)-indene-3-acetic acid, M.P. 228–230°. (R$_1$=hydrogen; R$_2$=CH$_3$; R$_3$=5-fluoro; R$_4$=6-fluoro; R$_5$=CH$_3$—SO—).

EXAMPLE 8

5,6-Difluoro-2-Methyl-1-(ρ-Methylsulfinylbenzylidene)-Indenyl-3-Acetic Acid (A) 3,4-difluorobenzaldehyde 57 g. (0.5 mole) of ortho-difluorobenzene in 250 ml. of methylene chloride is added to 100 g. (0.75 mole) of anhydrous aluminum chloride. The mixture is stirred (motor) and cooled in an ice bath while 85.5 g. (0.75 mole) of dichloromethyl methylether is added dropwise. Vigorous HCl evolution takes place, and the reaction mixture turns orange-red. After the addition, the mixture is stirred at room temperature for 15 minutes, and the liquid phase is decanted into 500 ml. of ice and water. The unreacted residue of aluminum chloride is washed with methylene chloride until colorless, and the washings are added to the water. The mixture is shaken well in a separation funnel until the methylene chloride layer is green. The organic layer is washed with saturated potassium carbonate solution until neutral, then dried (MgSO$_4$) and distilled to give 3,4-difluorobenzaldehyde, B.P. 70–74°/20 min. The dark residue in the distillation pot solidifies on cooling to give tris-(3-4, difluorophenyl)methane, M.P. 95–96°.

3,4-DIMETHYLBENZALDEHYDE

The above reaction of Example 6A is repeated except that o-xylene and dichloromethyl methylether are the starting materials. Using the same reaction conditions and techniques, there is obtained 3,4-dimethylbenzaldehyde.

4-MERCAPTOBENZALDEHYDE

The above reaction of Example 6A is repeated except that the starting materials are mercaptobenzene and dichloromethyl methylether. Using the same reaction conditions and techniques, there is obtained 4-mercaptobenzaldehyde.
(B) 5,6-difluoro-2-methyl-1-(ρ-methylsulfinylbenzylidene)-3-indenyl acetic acid The reactions of Examples 6B, 6C, 6D, 6E, 6F and 6G are repeated and 5,6-difluoro-2-methyl-1-(ρ-methylsulfinylbenzylidene)-3-indenyl acetic acid is obtained. ($R_1$=hydrogen; $R_2$=$CH_3$; $R_3$=5-fluoro; $R_4$=6-fluoro; $R_5$=$CH_3$—SO—).

Similarly, when 3,4-dimethylbenzaldehyde is used in the reactions in Example 8B, 5,6-dimethyl-2-methyl-1-(ρ-methylsulfinylbenzylidene)-3-indenyl acetic acid is obtained.

When 6-mercaptobenzaldehyde is used in the reactions in Example 8B, 6-mercapto-2-methyl-1-(ρ-methylsulfinylbenzylidene)-3-indenyl acetic acid is obtained.

EXAMPLE 9

α-(1-ρ-Methylsulfonylbenzylidene)-2-Methyl-5-Methoxy-6-Fluoro-3-Indenyl-Acetic Acid (A) 3-fluoro-4-methoxybenzaldehyde To a solution of o-fluoroanisole, 101 g. (0.80 mole) in 500 ml. dry methylene chloride is added dropwise over 30 minutes a solution of titanium tetrachloride, 182 g. (0.96 mole, 1.2 equiv.) and α,α-dichloromethylmethyl ether, 110 g. (0.96 mole) in an equal volume of methylene chloride. The temperature is maintained at 10–20° C. with an ice-bath. The mixture is stirred at room temperature for 1 hour longer and then poured over crushed ice-water with stirring. Ether (1 l.) is added, and the mixture stirred under nitrogen until solution occurs. The organic layer is extracted with water (3×), sodium bicarbonate solution (3×) and dried ($MgSO_4$). The solvent is evaporated off at 30° to give crude product as an oil. The oil is vacuum distilled through a jacketed Vigreoux column when it gives 3-fluoro-4-methoxybenzaldehyde, B.P. 120–121° C., at 10 mm. Hg; $R_f$ 0.6 on a silica-gel G plate with methylene chloride.
(B) 3-fluoro-4-methoxy-α-methylcinnamic acid A mixture of 3-fluoro-4-methoxybenzaldehyde, 34.2 g. (0.22 mole), propionic anhydride, 50 g. (0.38 mole) and sodium propionate, 21 g. (0.22 mole) is stirred under nitrogen at 150° C. for 15 hours. The reaction mixture is then poured into 1.3 l. of water with stirring, and the product is precipitated. 2.0 N potassium hydroxide solution (500 ml.) is added, and the mixture stirred for several hours, until the acid has dissolved.

The aqueous solution is extracted with ether (3×) and then acidified with concentrated hydrochloric acid with stirring. The precipitated product is collected, washed thoroughly with water and dried in a vacuum oven at 50° C. over potassium hydroxide pellets to give 3-fluoro-α-methyl-4-methoxycinnamic acid, M.P. 167–169° C.; $R_f$ 0.5 on silica-gel G with methylene chloride-methanol (1:1).
(C) 3-fluoro-4-methoxy-α-methyl dihydrocinnamic acid 3-Fluoro-4-methoxy-α-methylcinnamic acid (49.5 g.; 0.236 mole), in 800 ml. methanol is hydrogenated at 43 lbs. pressure and room temperature until the theoretical uptake of hydrogen has occurred (24 min at 20° C., using 1.5 g. platinum oxide catalyst). The solution is filtered and then evaporated with warming to 60° to give 3-fluoro-4-methoxy-α-methyl dihydrocinnamic acid $R_f$ 0.5 on silica-gel G with methylene chloride-methanol (9:1).
(D) 5-fluoro-6-methoxy-2-methylindanone A mixture of 3-fluoro-α-methyl-4-methoxy dihydrocinnamic acid, 49.3 g. (0.23 mole) in 500 g. of polyphosphoric acid is heated at 95° C. on a steam bath with occasional agitation for 75 min. The dark red solution is poured into 3.0 liters of water, and the mixture is stirred overnight. The precipitated product is collected, washed thoroughly with water and then taken up in ether. The ether solution is extracted with aqueous potassium bicarbonate (4×), diluted with methylene chloride, and dried ($MgSO_4$).

The organic solution is evaporated and recrystallized from methylene chloride-petroleum ether to give 5-fluoro-6-methoxy-2-methylindanone (M.P. 76–78°).
(E) Methyl 6-fluoro-5-methoxy-2-methyl-3-indenylacetate Into a 500 ml. three-necked flask fitted with mechanical stirrer, reflux condenser, drying tube, dropping funnel and nitrogen inlet is placed 8.0 g. zinc sheet and 100 ml. of dry benzene. A few milliliters of a solution of 21.3 g. (0.11 mole) of 5-fluoro-6-methoxy-2-methylindanone and 18.36 g. (0.121 mole) of methyl bromoacetate in 100 ml. of dry benzene is added at a time. A crystal of iodine is added. The mixture is gently heated with stirring. After the iodine color has disappeared, the remainder of the mixture is added gradually. The reaction is heated at reflux temperature for about 18 hours. The mixture is poured onto 600 ml. of 5% $H_3SO_4$ and about 500 g. of ice. Some ether is added. The organic layer is separated and washed with three portions of 5% $H_2SO_4$ water, $KHCO_3$ solution and finally water again. The organic layer is dried ($MgSO_4$) and concentrated to give 27.6 g. of reddish oil which crystallizes upon standing. Thin-layer chromatography on silica-gel G with methylene chloride methanol (99:1) shows product at $R_f$ (0.5).

Without further purification, the hydroxy ester is dehydrated to the indenylacetate. In 200 ml. of dry benzene, 14.2 g. (53 mole) of crude ester and 36 g. of phosphorus pentoxide are refluxed with stirring for ½ hour. After cooling, the reaction mixture is filtered and the solid residue washed well with benzene. The benzene filtrate is washed with two portions of salt water and dried ($MgSO_4$). The organic solution is concentrated and gives a slightly colored oil which rapidly crystallizes. The crude product is recrystallized from methylene chloride-petroleum ether to give methyl-6-fluoro-5-methoxy-2-methyl-3-indenyl-acetate (M.P. 61–62°).
(F) 6-fluoro-5-methoxy-2-methyl-1-(ρ-methylthiobenzylidene)-3-indenyl acetic acid To a solution of methyl-6-fluoro-5-methoxy-2-methyl-3-indenyl acetate, 9.3 g. (0.037 mole) and ρ-methylthiobenzaldehyde, 6.3 g. (1.1 equivalent) is added 16 ml. (2.0 equivalents) of 25% methanolic sodium methoxide. The mixture is stirred at reflux under nitrogen for 2 hours. An equal volume of water is added dropwise and refluxing continues for 30 minutes. The solution is cooled, diluted with water and extracted with ether (3×). Residual ether is blown off with nitrogen, and then the aqueous solution is acidified with 50% glacial acetic acid. The precipitated product is collected and washed thoroughly with water. The crude product is recrystallized from methanol to give 6-fluoro-5-methoxy-2-methyl-1-(ρ-methylthiobenzylidene)-2-indenyl acetic acid, M.P. 172–174°.
(G) 6-fluoro-5-methoxy-2-methyl-1-(ρ-methylthiobenzylidene)-3-indenyl acetic acid A solution of sodium periodate, 4.28 g. (20 mole) in 40 ml. of water is added dropwise to 6-fluoro-5-methoxy-2-methyl-1-(ρ-methylthiobenzylidene)-3-indenyl acetic acid, 3.70 g. (10 mole) in 300 ml. methanol and enough acetone to cause solution. This solution is stirred over night at room temperature and filtered. The filtrate is evaporated at 30° to a small volume which causes the product to precipitate. The suspension is diluted with several volumes of water, cooled and collected. After rinsing with water and cold methanol-water (1:1), the product is dried in vacuo over potassium hydroxide pellets, and then in a vacuum oven at 70° C. The crude product is recrystallized from methylene chloride-petroleum ether to give 6-fluoro-5-methoxy-2-methyl-1-(ρ-methylsulfinylbenzylidene)-3-indenyl acetic acid (M.P. 190–193°).

6-Fluoro-5-methoxy-2-methyl-1-(ρ-methylsulfonylbenzylidene)-3-indenyl acetic acid is prepared according to the procedure of Example 7 by the addition of 1.0 mole of m-chloroperbenzoic acid per mole of 6-fluoro-5-methoxy-2-methyl-1-(ρ-methylsulfonylbenzylidene)-3-indenyl acetic acid in an acetone solution.

α-[1-[(ρ-Methylsulfonylbenzylidene)-2-methyl-5-methoxy-6-fluoro-3-indenyl]-propionic acid is prepared by the procedures of Examples 3A, 3B and 3C. ($R_1$=hydrogen; $R_2$=$CH_3$; $R_5$=5—CH—O—; $R_4$=hydrogen; $R_5$=$CH_3$—$SO_2$—).

EXAMPLE 10

α-(1-ρ-Methylsulfonylbenzylidene)-2-Methyl-5-Fluoro-3-Indenyl-Acetic Acid (A) ρ-Fluoro-α-methylcinnamic acid ρ-Fluorobenzaldehyde (200 g., 1.61 mole), propionic anhydride (3.5 g., 2.42 mole) and sodium propionate (155 g., 1.61 mole) are mixed in a 1 l. three-necked flask which had been flushed with nitrogen. The flask is heated gradually in an oil-bath to 140°. After 20 hours, the flask is cooled to 100° and poured into 8 l. of water. The precipitate is dissolved by adding potassium hydroxide (302 g.) in 2.1 of water. The aqueous solution is extracted with ether, and the ether extracts washed with potassium hydroxide solution. The combined aqueous layers are filtered, acidified with concentrated HCl, filtered and the collected solid washed with water, thereby producing ρ-fluoro-α-methylcinnamic acid which is used as obtained.

(B) ρ-Fluoro-α-methylhydrocinnamic acid

To ρ-Fluoro-α-methylcinnamic acid (177.9 g., 0.987 mole) in 3.6 l. ethanol is added 11.0 g. of 5t Pd/C and the mixture is reduced at room temperature under a hydrogen pressure of 40 p.s.i. Uptake is 31/32 lbs. (97% of theoretical). After filtering the catalyst, the filtrate is concentrated in vacuo to give the product ρ-fluoro-α-methylhydrocinnamic acid used without weighing in next step.

(C) 6-Fluoro-2-methylindanone

To 932 g. polyphosphoric acid at 70° on the steam bath is added ρ-fluoro-α-methylhydrocinnamic acid (93.2 g., 0.5 mole) slowly with stirring. The temperature is gradually raised to 95° C., and the mixture kept at this temperature for 1 hour. The mixture is allowed to cool and added to 2 l. of water. The aqueous layer is extracted with ether, the ether solution washed twice with saturated sodium chloride solution, 5% $Na_2CO_3$ solution, water, and then dried. The ether filtrate is concentrate with 200 g. silica-gel, and added to a five pound silica-gel column packed with 5% ether-petroleum ether. The column is eluted with 5–10% ether-petroleum ether and followed by tlc to give 6-fluoro-2-methyl-inanone.

(D) 5-Fluoro-2-methylindanone-3-acetic acid

A mixture of 6-fluoro-2-methylindanone (18.4 g., 0.112 g. mole), cyanoacetic acid (10.5 g., 0.123 mole), acetic acid (6.6 g.), and ammonium acetate (1.7 g.) in dry toluene (15.5 ml.) is refluxed with stirring for 21 hours, as the liberated water is collected in a Dean Stark trap. The toluene is concentrated, and the residue dissolved in 60 ml. of hot ethanol and 14 ml. of 2.2 N. aqueous potassium hydroxide solution. 22 g. of 8.5% KOH in 150 ml. of water is added, and the mixture refluxed for 13 hours under nitrogen. The ethanol is removed under vacuum, 500 ml. water added, the aqueous solution washed well with ether and then boiled with charcoal. The aqueous filtrate is acidified to pH 2 with 50% hydrochloric acid, cooled and the precipitate collected. In this way dried 5-fluoro-2-methylindenyl-3-acetic acid (M.P. 164–166°) is obtained.

(E) 5-Fluoro-2-methyl-1-(ρ-methylthiobenzylidene)-3-indenyl acetic acid 5-fluoro-2-methyl-3-indenyl acetic acid (15 g., 0.072 mole) ρ-methylthiobenzaldehyde (14.0 g., 0.091 mole) and sodium methoxide (13.0 g., 0.24 mole) are heated in methanol (200 ml.) at 60° under nitrogen with stirring for 6 hours. After cooling, the reaction mixture is poured into 750 ml. of ice-water, acidified with 2.5 N hydrochloric acid, and the collected solid triturated with a little ether to produce 5-fluoro-2-methyl-1-(ρ-methylthiobenzylidene)-3-indenyl acetic acid (M.P. 187–188.2°). U.V. in methanol $\lambda_{max}$, 348 mμ (E % 500), 258 (557), 258 (495), 353 (513), 262.5 (577), 242.5 (511).

(F) 5-Fluoro-2-methyl-1-(ρ-methylthiobenzylidene)-3-indenyl acetic acid

To a solution of 5-fluoro-2-methyl-1-(ρ-methylthiobenzylidene)-3-indenyl acetic acid (3.4 g., 0.01 mole) in a mixture of methanol (250 ml.) and acetone (100 ml.) is added a solution of sodium periodate (3.8 g., 0.018 mole) in water (50 ml.) with stirring.

Water (450 ml.) is added after 18 hours, and the organic solvents removed under vacuum below 30°. The precipitated product is filtered, dried and recrystallized from ethyl acetate to give 5-fluoro-2-methyl-1-(ρ-methylthiobenzylidene)-3-indenyl acetic acid. Upon repeated recrystallization upon ethyl-acetate there is obtained cis-5-fluoro-2-methyl-1-(ρ-methylthiobenzylidene)-3-indenyl acetic acid, M.P. 184–186°. U.V. in methanol; $\lambda_{max}$ 328 (E % 377), 286 (432), 257.5 shldr. (413), 227 (548).

Further runs reveal the existence of a second polymorph of cis-5-fluoro-2-methyl-1-(ρ-methylthiobenzylidene)-3-indenyl acetic acid, M.P. 179–181° C.

5-chloro-2-methyl-1-(ρ-methylthiobenzylidene)-3-indenyl acetic acid is prepared by the procedure as described in Example 10.

5-fluoro-2-methyl-1-(ρ-methylthiobenzylidene)-3-indenyl acetic acid is prepared according to the procedure of Example 7 by the addition of 1.0 mole of m-chloroperbenzoic acid per mole of 5-fluoro-2-methyl-1-(pmethyl-sulfinylbenzylidene)-3-indenyl acetic acid in an acetone solution.

α-[1-(ρ-Methylsulfonylbenzylidene)-2-methyl-5-fluoro-3-indenyl]-propionic acid are prepared by the procedures of Examples 3A, 3B and 3C. ($R_1$=hydrogen; $R_2$=$CH_3$; $R_3$=5-fluoro; $R_4$=hydrogen; $R_5$=$CH_3SO_2$—).

EXAMPLE 11

Cis-5,7-Difluoro-2-Methyl-1-(ρ-Methylsulfinylbenzylidene)-3-Indenyl Acetic Acid (A) 2,4-difluorobenzaldehyde A 250 ml., three-necked flask is fitted with a stirrer, a thermometer, a dropping funnel with a long stem to the bottom of the flask and a reflux condenser with a tube leading to the back of a hood. 50 g. (0.38 mole) of 2,4-difluorotoluene is heated to reflux with stirring and irradiated with a Hanovia ultraviolet lamp. 41.5 ml. of bromine is gradually added. The reaction is completed in 2.5 hours during which time the reflux temperature rises from 112° to 155°.

A 2 l. three-necked flask is fitted with a stirrer and reflux condenser. In the flask is placed 200 ml. of water and 140 g. calcium carbonate. The cooled above-described reaction mixture is transferred using some ether for rinsing. The hydrolysis is completed by refluxing with stirring for 18 hours. The aldehyde is isolated by steam distillation from the reaction flask. The oil is separated and the aqueous phase is extracted once with ether. The combined oil and ether extract is dried over anhydrous $MgSO_4$ and concentrated under reduced pressure to leave 2,4-difluorobenzaldehyde, still containing some ether which is distilled through a short Vigreux column under reduced pressure and separated into several fractions. These are combined to give 2,4-difluorobenzaldehyde, B.P. 56–58° 12 mm.

(B) 2,4-difluoro-α-methylcinnamic acid

A 500 ml., three-necked flask is fitted with reflux condenser, drying tube, stirrer and $N_2$ inlet. To a mixture of 55.4 g. (0.39 mole) of 2,4-difluorobenzaldehyde and 56 ml. of propionic anhydride is added 38 g. (0.39 mole) of sodium propionate. The reaction mixture is heated at 135–140° (oil bath temp.) for 19 hours with stirring under nitrogen. The still warm solution is poured into 1 l. of water with stirring. A solid separates, which upon adding 56 g. of potassium hydroxide, dissolves. The solution is extracted with ether, and then heated on the steam bath to remove the ether. After cooling in an ice-bath, concentrated hydrochloric acid is added with stirring. The product which separates is collected and washed with cold water. After drying at 60° over KOH, 2,4-difluoro-α-methylcinnamic acid, M.P. 126–128° is obtained.

(C) 2,4-difluoro-α-methylcinnamic acid

In 800 ml. of methanol, 60 g. (0.3 mole) of 2,4-difluoro-α-methylcinnamic acid with 1.5 g. of platinum oxide catalyst is shaken under an initial pressure of 42 lbs. of hydrogen until one equivalent of hydrogen is absorbed. The reaction time is 30 minutes. The catalyst is removed by filtration and washed with methanol. The methanol, when evaporated off, leaves near colorless 2,4-difluoro-α-methyldihydrocinnamic acid as an oil which is used in the next step without further purification.

(D) 4,6-difluoro-2-methylindanone

A solution of 2,4-difluoro-α-methyldihydrocinnamic acid, 54.8 g. (0.274 mole) in 125 ml. thionyl chloride is stirred for 90 minutes, and then at reflux for 90 minutes longer. The reaction solution is evaporated under reduced pressure leaving the acid chloride product as an oil.

To a suspension of ice-bath cooled anhydrous powdered aluminum chloride, 60 g. (0.45 mole), in 250 ml. of dry carbon disulfide is added dropwise over 10 minutes, a solution of the acid chloride, 60 g., in 100 ml. carbon disulfide. After the addition, the ice bath is removed, and the temperature raised slowly to room temperature. The mixture is stirred at room temperature for 20 hours, and then is poured into 2 l. of 10 aqueous hydrochloric acid-crushed ice with stirring. Ether is added, and the stirring continued until everything dissolves. The ether layer is extracted with 5% hydrochloric acid (2×), water (2×), and sodium bicarbonate solution (2×), when it is diluted with methylene chloride and dried ($MgSO_4$). The filtered solution is evaporated with warming to 70° C. to give the crude 4,6-difluoro-α-methylindanone as an oil which crystallizes on standing. The crude product is purified by chromatography of a column (7.0×35 cm.) of silica-gel, 400 g. of J. T. Baker 3405 packed in petroleum ether-methylene chloride (2:1). The column is developed and eluted with the same solvent system, and upon recrystallization from methylene chloride-petroleum ether gives 4,6-difluoro-2-methylindanone, M.P. 68–69° C.

(E) Methyl 5,7-difluoro-2-methylindenyl-3-acetate

About 20% of a solution containing 4,6-difluoro-2-methylindanone, 15.0 g. (83 mole), and methyl bromoacetate, 14.0 g. (1.1 equiv.) in 100 ml. dry benzene is added to a stirred suspension of powdered zinc dust (Merck dried 120°/22 mm.), 6.5 g. (1.2 equiv.) in 74 ml. dry benzene under a nitrogen atmosphere. Several crystals of iodine are added, and the mixture slowly brought to a reflux. The remainder of the solution is added dropwise over 10 minutes, and the mixture stirred at reflux overnight, i.e., 17 hours. The reaction is cooled to room temperature, the mixture poured into 2.0 l. of 20% aqueous sulfuric acid-crushed ice with stirring, and ether added until a clear solution is obtained. The ether layer is extracted with 5% aqueous sulfuric acid (3×), water (3×), diluted with methylene chloride and dried ($MgSO_4$). The filtered etheral solution is evaporated to give crude hydroxy ester.

Powdered phosphorus pentoxide (60.0 g.) is added to the hydroxy ester (20.0 g.) in 400 ml. of dry benzene. The mixture is stirred at reflux for 30 minutes, and the clear benzene solution decanted. The residue is rinsed with benzene and then with ether. The combined organic solutions are diluted with ether, extracted six times with aqueous sodium sulfate solution, twice with aqueous potassium bicarbonate solution, diluted with methylene chloride and dried ($MgSO_4$). The crude indenyl acetate product is obtained by evaporation of the filtered elution to give an oil. The product is crystallized from petroleum ether and gives methyl 5,7-difluoro-2-methylindenyl-3-acetate, M.P. 69–70° C.

(F) 5,7-difluoro-2-methyl-1-(ρ-methylthiobenzylidene)-3-indenyl acetic acid, a mixture of geometric isomers Powdered sodium methoxide, 2.2 g. (40 mole) is added to a suspension of methyl 5,7-difluoro-2-methyl-indenyl-3-acetate (4.78 g.) (20 mole) and ρ-methylthiobenzaldehyde, 3.35 g. (22 mole), in 40 ml. dry methanol under nitrogen. A clear solution results which is refluxed for 60 minutes. An equal volume of water is added, and refluxing continued under nitrogen for 30 minutes to complete saponification. The solution is diluted with several volumes of water and extracted with ether. Nitrogen is bubbled through the aqueous solution to remove the residual ether solvent. Fifty percent aqueous acetic acid (40 ml.) is used to precipitate the product. The product is collected and washed well with water. Then it is dried in a desiccator over potassium hydroxide pellets, and finally in the oven at 100°. The crude product is recrystallized from methylene chloride-petroleum ether and gives a mixture of the cis and trans isomers of the acid, M.P. 164–173° in a 1:3 ratio, identifiable by integrating the 2-$CH_3$ signal in the N.M.R. spectra at 7.82γ for cis and 8.20γ for trans.

(G) Cis-methyl-5,7-difluoro-2-methyl-1-(ρ-methylthiobenzylidene)-3-indenyl-acetate isolation by column chromatography Four drops of concentrated sulfuric acid are added to a solution of 5,7-difluoro-2-methyl-1-(ρ-methylthiobenzylidene)-3-indenyl acetic acid, 1.0 g. (2.8 mole) in 60 ml. of dry methanol, and the solution stirred at reflux overnight. The solution is cooled and crystals separated which are collected, rinsed with cold methanol-water (1:1) and dried over potassium hydroxide pellets. These crystals are found to be about 95% of the trans-isomer, and could be further purified by recrystallizing from methanol giving the trans-isomer, M.P. 106–106.5° C. Powdered potassium bicarbonate is added to the filtrate from the first crop of crystals, followed by water. A second crop of mixed ester is obtained in this way which is cis-enriched and used for chromatography.

1.7 g. of cis and trans-mixed esters are chromatographed on a column (3.0×90 cm.) of silica-gel, 250 g. of J. T. Baker 3405, packed in methylene chloride-petroleum ether (1:9). The column is developed and eluted with a 1:4 ratio of the same solvents. 0.3 to 0.4 l. cuts are taken as the yellow bands are eluted. In this way the trans-isomer and the cis-isomer (M.P. 94–94°) are obtained; U.V. of trans in MeOH $_{max}$ 217 m$\mu$, 256 and 362 m$\mu$; U.V. of cis-isomer in MeOH $\lambda$max $_{218}$ m$\mu$, 260 and 357 m$\mu$.

(H) Cis-5,7-difluoro-2-methyl-1-(p-methylthiobenzylidene)-3-indenyl acetic acid 1.0 N aqueous sodium hydroxide 3.0 ml. (3.0 mole) is added to cis-methyl 5,7-difluoro-2-methyl-1-(p-methylthiobenzylidene)-3-indenylacetate, 250 mg. (0.64 mole) in 20 ml. methanol under nitrogen. The mixture is refluxed for 1 hour, cooled, diluted with water and acidified with several ml. of 50% acetic acid. Crystals form and after further chilling in ice bath, they are collected, worked thoroughly with water and sucked nearly dry. The product is recrystallized form methanol-water, dried over potassium hydroxide pellets in a vacuum desiccator and finally in a vacuum oven at 100°. In this way cis-5,7-difluoro-2-methyl-1-(p-methylthiobenzylidene)-3-indenyl acetic acid (M.P. 182–184°) is obtained.

(I) Cis-5,7-difluoro-2-methyl-1-(p-methylsulfinylbenzylidene)-3-indenyl acetic acid Sodium periodate 214 mg. (1.0 mole) in 2 ml. water is added to cis-5,7-difluoro-2-methyl-1-(p-methylsulfinylbenzylidene)-3-indenyl acetic acid, 170 mg. (0.475 mole) in 12 ml. of methanol and about 0.5 ml. acetone at room temperature. The mixture is stirred overnight when inspection of tlc on silica-gel G using methylene chloride-methanol elution (1:1) shows that there is no starting material present but a trace of sulfone at $R_f$ 0.55. The reaction mixture is filtered and concentrated to a small volume without heating and diluted with water. The product is collected, rinsed with water and dried over potassium hydroxide pellets in a vacuum desiccator and finally in the oven desiccator at 80°. The product is recrystallized from ethyl acetate-petroleum ether and gives pure cis-5,7-difluoro-2-methyl-1-(p-methylsulfinylbenzylidene)-3-indenyl acetic acid, M.P. 188–189° C. ($R_1$=hydrogen; $R_2$=CH; $R_3$=5-fluoro; $R_4$=7-fluoro; $R_5$=CH$_3$SO).

EXAMPLE 12

α-(1-Methylsulfinylbenzylidene-2-Methyl-5,6-Difluoro-3-Indenyl)-Propionic Acid

α-[1-(p-methylsulfinylbenzylidene)-2-methyl-5,6-difluoro-3-indenyl]-propionic acid (0.01 mol.) is prepared by the procedures of Examples 3A, B and C. The procedure yields the desired compound ($R_1$=hydrogen; $R_2$=CH$_3$; $R_3$=5-fluoro; $R_4$=6-fluoro; $R_5$=CH$_3$SO).

EXAMPLE 13

α-(1-ρ-Methylsulfinylbenzylidene-2-Methyl-5-Fluoro-6-Methoxy-3-Indenyl)-Propionic Acid α-[1-(ρ-methylsulfinylbenzylidene)-2-methyl-5-fluoro-6-methoxy-3-indenyl]-propionic acid is prepared by the procedures of Examples 3A–3C ($R_1$=methyl; $R_2$=methyl; $R_3$=5-fluoro; $R_4$=6-methoxy; $R_5$=CH$_3$—SO).

EXAMPLE 14

α-(1-ρ-Methylsulfinylbenzylidene-2-Methyl-5-Fluoro-3-Indenyl)-Propionic Acid

α-[1-(ρ-methylsulfinylbenzylidene)-2-methyl-5-fluoro-3-indenyl]-propionic acid is prepared by the procedures of Examples 3A–3C ($R_1$=methyl; $R_2$=methyl; $R_3$=5-fluoro; $R_4$=hydrogen; $R_5$=CH$_3$—SO).

EXAMPLE 15

N-[5-fluoro-2-methyl-1-(ρ-methylsulfinyl-benzylidene)-3-indenylacetyl]glycine (A) Benzyl-N-[5-fluoro-2-methyl-1-(ρ-methylsulfinylbenzylidene)-3-indenylacetyl]-glycinate. The procedure of Example 14 is followed using benzylamine acetate in place of the morpholine to produce the above-named compound.

(B) N-[5-fluoro-2-methyl-1-(ρ-methylsulfinylbenzylidene)-3-indenylacetyl]-glycine. Benzyle-N-(5-fluoro-2-methyl-1-(ρ-methylsulfinylbenzylidene)-3-indenylacetyl]-glycinate (0.03 mole) in a mixture of 25 ml. of anhydrous ethanol and 2.5 ml. of 1 N sodium hydroxide is allowed to stand at room temperature for 18 hours. The solution is diluted with water and extracted with ether. The aqueous layer is acidified with dilute hydrochloric acid and the organic product is extracted with ethyl acetate, washed with water and dried over sodium sulfate. Evaporation of the solution gives N-[5-fluoro-2-methyl-1-(ρ-methylsulfinylbenzylidene)-3-indenylacetyc acid, the corresponding indenyl acyl glycine is obtained.

EXAMPLE 16

(A) Sodium 5-fluoro-2-methyl-1-(ρ-methylsulfinyl-benzylidene)-3-indenylacetate 5-fluoro-2-methyl-1-(ρ-methylsulfinylbenzylidene)-3-indenylacetic acid (1.79 g.) in methanol (10 ml.) is added to a solution of sodium methoxide (0.27 g.) in methanol (5 ml.). The reaction mixture is stirred for 20 minutes and evaporated to dryness to yield sodium 5-fluoro-2-methyl-1-(ρ-methylsulfinylbenzylidene)-3-indenylacetate.

(B) Calcium 5-fluoro-2-methyl-1-(ρ-methylsulfinylbenzylidene)-3-indenylacetate

The above reaction is repeated using 2 moles of acid per mole of calcium methoxide. Using the same reaction conditions and techniques there is obtained calcium 5-fluoro-2-methyl-1-(ρ-methylsulfinylbenzylidene)-3-indenylacetate.

EXAMPLE 17

5-Methoxy-2-Methyl-1-(ρ-methyl-sulfonylbenzylidene)-3-indenyl-y-trans-crotonic acid According to procedures C & D in Example 1, 6-methoxy-2-methylindanone is allowed to react with γ-bromocrotonic acid methyl ester to give the desired methylthio product.

Similarly, if any of the other indanones listed in Table I and synthesized according to Example 2 are used in the above procedure with either γ-bromocrotonic acid methyl ester or with γ-bromo-γ-methyl-crotonic acid methyl ester, the corresponding indenylcrotonic acids are obtained. All of these are oxidized from methylthio to methyl sulfonyl compounds with periodate according to Example 1E.

EXAMPLE 18

5-methoxy-2-methyl-1-(ρ-methylsulfonylcinnamilydene)-3-indenyl-acetic acid

According to procedure D in Example 1, methyl 5-methoxy-2-methyl-3-indenyl acetate is condensed with ρ-methylthio cimamldehyde to give the desired methylthio product, which can be oxidized according to procedure 1E to the title compound.

Similarly, if other 3-indenyl acetates, propionates or crotonates (See Example 17) are used, the corresponding sulfonyl compounds are obtained, after oxidation of the intermediate methylthio compounds according to Example 1E.

EXAMPLE 19

α-(1,-p-Methylsulfonylbenzylidene)-2-Methyl-5-Fluoro-3-Indenyl-Acetic Acid Methyl Ester 5-fluoro-2-methyl-1-(p-methylsulfonylbenzylidene)-3-indenyl acetic acid is prepared by the procedure of Example 10, and converted to the methyl ester derivative by the following procedure. Sodium methoxide (4.4 M in methanol, 1.36 ml, 0.006 mol) is added to a stirred cooled solution (0° C.) of 5-fluoro-2-methyl-1-(p-methylsulfonylbenzylidene)-3-indenyl acetic acid (1.04 g, 0.0028 ,p;) in methanol (5 ml) and acetonitrile (10 ml). After 30 min, the reaction mixture is dropped into concentrated hydrochloric acid (50 ml) and extracted with methylene chloride (3×25 ml). The organic layer is extracted with saturated sodium bicarbonate (3×25 ml), dried with sodium sulfate, and concentrated in vacuo. The resulting oil is crystallized from tetrahydrofuran/hexane to yield 0.2 g of the desired compound. The melting point is 165–166° C. ($R_1$=hydrogen; $R_2$=$CH_3$; $R_3$=5-fluoro; $R_4$=hydrogen; $R_5$=$CH_3SO_2$—; M=$OCH_3$) Other methyl esters of compounds of this invention can be prepared in a similar fashion.

The following Examples 20–31 are of compounds of Formula II.

EXAMPLE 20

4,8-Dianilino Pyrimido-Pyrimidine

This compound was prepared from 2,6-dichlor-4,8-dianilino pyrimido-pyrimidine by a reaction with hydrogen iodide and phosphorus diiodide.

12 gm. of phosphorus diiodide ($P_2I_4$) were added in small portions to a suspension, heated on a steam bath, of 3.8 gm. (0.01) 2,6-dichloro-4,8-dianilino pyrimido-pyrimidine in 40 cc. hydrogen iodide (d=1.7) in the course of about half an hour. Heating was continued for one hour. The mixture was then cooled and the precipitated crystals were filtered off on a vacuum filter. The precipitate was extracted with 200 cc. of hot dioxane. 2.8 gm. of red, brilliant rhombic crystals remained after extraction. The yield was about 90% of the theoretical yield. The crystals were twice recrystallized from dimethyl formamide, whereby very slightly yellowish, small needles having a melting point of 255–256° C. were obtained.

EXAMPLE 21

2,6-Dichloro-4,8-Diamino Pyrimido-Pyrimidine Compounds

Such compounds were obtained by reacting tetrachloro pyrimido-pyrimidine at room temperature with various amines.

(a) 2,6-dichloro-4,8-di-(N-hydroxy ethyl anilino) pyrimido-pyrimidine: 10.0 gm. (0.08 mol) N-hydroxy ethyl aniline, dissolved in 15 cc. dioxane, were poured into a solution of 5.4 gm. (0.02 mol) 2,4,6,8-tetrachloro pyrimido-pyrimidine in 50 cc. dry dioxane, while stirring. A yellowish crystalline precipitate rapidly separated out, accompanied by a slight generation of heat. The precipitate evidently consisted essentially of N-hydroxy-ethyl-aniline hydrochloride. 200 cc. water were added to the resulting suspension. The hydrochloride went into solution and, simultaneously, 2,6-dichloro-4,8-di-(N-hydroxy ethyl-anilino) pyrimido-pyrimidine was precipitated in the form of a yellow precipitate which was at first somewhat sticky but rapidly solidified. The yield amounted to 8.1 gm., corresponding to 86% of the theoretical yield. For analytical purposes the compound was repeatedly recrystallized from methanol, thereby yielding a bright yellow microcrystalline powder consisting of small prisms. Its melting point was 189–190° C.

The following 2,6-dichloro-4,8-diamino pyrimido-pyrimidine compounds were prepared by proceeding in an analogous manner as described above under (a):

(b) With morpholine: 2,6-dichloro-4,8-dimorpholino pyrimido-pyrimidine, melting point: 276–277° C.

(c) With p-chloro-aniline: 2,6-dichloro-4,8-di-(p-chloro anilino) pyrimido-pyrimidine, melting point: 307–309° C.

(d) With β-hydroxy-ethylamine: 2,6-dichloro-4,8-di(β-hydroxy ethylamino) pyrimido-pyrimidine, melting point: 246–248° C.

(e) With β-diethylamino-ethylamine: 2,6-dichloro-4,8-bis (β-diethylamino ethylamino) pyrimido-pyrimidine, melting point: 128–130° C.

(f) With methyl-dodecyl-amine: 2,6-dichloro-4,8-bis-(methyl dodecylamino) pyrimido-pyrimidine, melting point: 76–77° C.

(g) With isoamyl-amine: 2,6-dichloro-4,8-bis-(isoamylamino) pyrimido-pyrimidine, melting point: 94–95° C.

(h) With benzylamine: 2,6-dichloro-4,8-bis-(benzylamino) pyrimido-pyrimidine, melting point: 229–230° C.

(i) With p-dimethylamino-aniline: 2,6-dichloro-4,8-bis-(p-dimethylamino aniline) pyrimido-pyrimidine, melting point: did not melt at or below 350° C.

(j) With diallylamine: 2,6-dichloro-4,8-bis-(diallylamino) pyrimido-pyrimidine, melting point: 100–101° C.

(k) With methyl-cyclohexyl-amine: 2,6-dichloro-4,8-di-(methyl cyclohexyl amino) pyrimido-pyrimidine, melting point: 179–181° C.

(l) With β-chloro-ethylamine: 2,6-dichloro-4,8-di-(β-chloro ethylamino) pyrimido-pyrimidine: did not melt at temperatures up to 350° C.

(m) With butyl-ethanolamine: 2,6-dichloro-4,8-bis-(butylethanolamino) pyrimido-pyrimidine, melting point: 140–141° C.

(n) With benzyl-ethanolamine: 2,6-chloro-4,8-bis-(benzyl-ethanolamino) pyrimido-pyrimidine, melting point: 173–175° C.

(o) With 2,3-dihydroxy-propylamine: 2,6-dichloro-4,8-bis-(2,3-dihydroxy-propylamino) pyrimido-pyrimidine, melting point 208–210° C.

(p) With ammonia: 2,6-dichloro-4,8-diamino pyrimido-pyrimidine: did not melt at 350° C. or below.

(q) With carbethoxy-methylamine: 2,6-dichloro-4,8-di-(carbethoxy-methylamino) pyrimido-pyrimidine, melting point: 207–209° C. with decomposition.

EXAMPLE 22

2,6-Dichloro-4,8-Dianilino Pyrimido-Pyrimidine

This compound was prepared from 2,6-dichloro-4,8-diiodo pyrimido-pyrimidine and aniline.

4.5 gm. (0.01 mol) 2,6-dichloro-4,8-diiodo pyrimido-pyrimidine were dissolved in 100 cc. dry dioxane. The solution was added dropwise, while stirring and cooling with ice, to a solution of 3.7 gm. (0.04 mol) aniline in anhydrous benzene in the course of half an hour. Yellow crystals started to precipitate out very rapidly. Stirring was continued for half an hour. The precipitated crude product was filtered off on a vacuum filter, triturated with slightly acid water (dilute hydrochloric acid), again filtered on a vacuum filter, washed and dried. 2.3 gm., corresponding to 61% of the theoretical yield, were obtained. For analytical purposes, the compound was recrystallized three times from dioxane, whereby very slightly yellowish, small needles having a melting point of 287–288° C. were obtained.

EXAMPLE 23

2,4,6,8-Tetraanilino Pyrimido-Pyrimidine

This compound was prepared from 2,4,6,8-tetrachloro pyrimido-pyrimidine and aniline.

2.7 gm. (0.01 mol) tetrachloro pyrimido-pyrimidine, having a melting point of 255–258° C., were refluxed with 45 gm. aniline for 25 minutes. On pouring the resulting dark brown solution into 500 cc. of 1 N hydrochloric acid, crude tetraanilino pyrimido-pyrimidine precipitated out in the form of a brownish amorphous precipitate. Yield: 4.0 gm. corresponding to 80% of the theoretical yield. The compound was recrystallized three times from dioxane, whereby canary yellow, small needles having a melting point of 300–302° C. were obtained.

Said compound was also obtained by proceeding in the same manner but refluxing the following compounds with aniline:
2,6-dichloro-4,6-dianilino pyrimido-pyrimidine,
2,6-dichloro-4,8-diamino pyrimido-pyrimidine,
2,6-dichloro-4,8-dihydroxy pyrimido-pyrimidine, and
2,6-dichloro-4,8-dipiperidino pyrimido-pyrimidine.

The starting material, 2,4,6,8-tetrachloro pyrimido-pyrimidine, was obtained by refluxing 2,6-dichloro-4,8-dihydroxy pyrimido-pyrimidine with phosphorous oxychloride.

EXAMPLE 24

6-Chloro-4,8-Dimorpholino Pyrimido-Pyrimidine

This compound was obtained from 6-chloro-4,8-diiodo pyrimido-pyrimidine and morpholine.

A mixture of 2.0 gm. (0.023 mol) morpholine and 2.0 gm. (0.02 mol) triethylamine, dissolved in 20 cc. dioxane, was added to a solution of 4.2 gm. (0.01 mol) 6-chloro-4,8-diiodo pyrimido-pyrimidine in 50 cc. dioxane, while stirring and cooling. The mixture was allowed to stand for about half an hour. Subsequently, 400 cc. water were added thereto. The initially precipitated morpholine hydrochloride was again dissolved by addition of water, and crude 6-chloro-4,8-dimorpholino pyrimido-pyrimidine precipitated out. Yield: 2.7 gm. corresponding to 80% of the theoretical yield.

For analytical purposes, the compound was recrystallized three times from dioxane and yielded long colorless needles having a melting point of 199–200 C.

The starting material, 6-chloro-4,8-diiodo pyrimido-pyrimidine was prepared by reacting 4,6,8-trichloro pyrimido-pyrimidine with sodium iodide.

EXAMPLE 25

4,6,8-Triamino pyrimido-Pyrimidine Compounds

These compounds were prepared by reacting 6-chloro-4,8-diamino pyrimido-pyrimidine compounds with various amines at elevated temperature and, if required, under pressure.

(a) 6-morpholino-4,8-bis-(diethylamino) pyrimido-pyrimidine: 6 gm. (about 0.02 mol) 6-chloro-4,8-bis(diethylamino) pyrimido-pyrimidine were heated in a sealed tube with 3.4 gm. (0.04 mol) morpholine to 180° C. for one and a half hours. The pasty reaction product was obtained in solid form only after reprecipitating it twice from very dilute hydrochloric acid and allowing it to stand for a prolonged period of time. 2.8 gm. were obtained on drying in a vacuum at rom temperature. For analytical purposes, the compound was recrystallized twice from a mixture of methanol and water (2:1) whereby ivory-colored, lustrous scales (small irregular leaflets) having a melting point of 73–75° C. were obtained.

The following 4,6,8-triamino-pyrimido-pyrimidine compounds were obtained by proceeding in a manner analogous to that described above under (a), but using different amines:

(b) 6-methylamino-4,8-bis-(ethylamino)-pyrimido-pyrimidine having a melting point of 94–96° C. from 6-chloro-4,8-bis-(ethylamino)-pyrimido-pyrimidine and methylamine.

(c) 6-morpholino-4,8-di-(ethyl-ethanol-amino)-pyrimido-pyrimidine having a melting point of 120–122° C. from 6-chloro-4,8-di-(ethyl-ethanolamino)-pyrimido-pyrimidine and morpholine.

(d) 6-anilino-4,8-diamino-pyrimido-pyrimidine having a melting point of 170–173° C. from 6-chloro-4,8-diamino-pyrimido-pyrimidine and aniline.

(e) 6-diethanolamino-4,8-bis-(allylamino)-pyrimido-pyrimidine having a melting point of 104–106° C. from 6-chloro-4,8-bis-(allylamino)-pyrimido-pyrimidine and diethanolamine.

(f) 6-dimethylamino-4,8-diamino-pyrimido-pyrimidine having a melting point of 292–292° C. from 6-chloro-4,8-diamino-pyrimido-pyrimidine and dimethylamine.

(g) 6-diethanolamino-4,8-dipiperidyl-pyrimido-pyrimidine having a melting point of 100–105° C. (sintering started at 95° C.) from 6-chloro-4,8-dipiperidyl-pyrimido-pyrimidine and diethanolamine.

(h) 6-($\beta$-hydroxy-ethylamino)-4,8-dimorpholyl-pyrimido-pyrimidine having a melting point of 106–108° C. from 6-chloro-4,8-dimorphoyl-pyrimido-pyrimidine and methyl-ethanolamine.

(i) 6-methyl-ethanolamino-4,8-bis-(methylamino)-pyrimido-pyrimidine having a melting point of 64–66° C. from 6-chloro-4,8-bis-(methylamino)-pyrimido-pyrimidine and methyl-ethanolamine.

(j) 6-morpholyl-4,8-di-(3-methoxypropyl-amino)-pyrimido-pyrimidine having a melting point of 80–82° C. from 6-chloro-4,8-di-(3-methoxypropyl-amino)pyrimido-pyrimidine and morpholine.

(k) 6-diisopropanolamino-4,8-dimorpholyl-pyrimido-pyrimidine having a melting point of 106–108° C. from 6-chloro-4,8-dimorpholyl-pyrimido-pyrimidine and diisopropanolamine.

(l) 6-diethanolamino-4,8-di-(p-nitro-amilino)-pyrimido-pyrimidine having a melting point of 310–311° C. from 6-chloro-4,8-di-(p-nitro-anilino)-pyrimido-pyrimidine and diethanolamine.

(m) 6-piperidino-4,8-di-($\beta$-hydroxy-ethylamino-pyrimido-pyrimidine having a melting point of 178–179° C. from 6-chloro-4,8-di-($\beta$-hydroxy-ethylamino)-pyrimido-pyrimidine and piperidine.

(n) 6-diethanol amino-4,8-dimorpholyl-pyrimido-pyrimidine having a melting point of 150–152° C. from 6-chloro-4,8-dimorpholyl-pyrimido-pyrimidine and diethanolamine.

(o) 6-morpholyl-4,8-bis-(ethylamino)-pyrimido-pyrimidine having a melting point of 151–153° C. from 6-chloro-4,8-bis-(ethylamino)-pyrimido-pyrimidine and morpholine.

(p) 6-morpholyl-4,8-diamino-pyrimido-pyrimidine having melting point of 266–267° C. from 6-chloro-4,8-diamino-pyrimido-pyrimidine and morpholine.

EXAMPLE 26

2,4,6,8-Tetraamino-Pyrimido-Pyrimidine Compounds

These compounds were prepared by reacting 2,4,6,8-tetrachloro-pyrimido-pyrimidine with various amines at elevated temperature and, if required, under pressure and in the presence of copper powder or copper salts as reaction acceleration.

(a) 2,4,6,8-tetra-(dimethylamino)-pyrimido-pyrimidine: 2.7 gm. (0.01 mol) tetrachloro-pyrimido-pyrimidine were added in small portions, while stirring, to 50 cc. of a dimethylamine solution in absolute ethanol (containing 0.14 mol of dimethyl-amine), whereby the dichloro diamino compound precipitated out. 0.1 gm. copper sulfate was added to the resulting suspension and the mixture was heated in a sealed, thick-walled glass tube to 200° C. for one hour. The reaction solution was diluted with water and the crude reaction product was reprecipitated by dissolving it in 200 cc. 0.2 N hydrochloric acid, purifying the solution with animal charcoal, and precipitating the reaction product with concentrated ammonia. Yield: 1.7 gm. corresponding to 56% of the theoretical yield. For analytical purposes, the compound was recrystallized three times from absolute ethanol and dried at 130° C. in a vacuum of 0.1 mm. Bright yellow, irregular needles having a melting point of 164–165° C. were obtained.

The following 2,4,6,8-tetraamino-pyrimido-pyrimidine compounds were prepared by following the procedure described above under (a), but reacting tetrachloro-pyrimido-pyrimidine with various other amines, as indicated:

(b) With allylamine: 2,4,6,8-tetra-(allylamino)-pyrimido-pyrimidine having a melting point of 201–202° C.

(c) With methyl-ethanolamine: 2,4,6,8-tetra-(methyl ethanolamino)-pyrimido-pyrimidine having a melting point of 155–156° C.

(d) With β-hydroxy-ethyl amine: 2,4,6,8-tetra-(β-hydroxy-ethylamino)-pyrimido-pyrimidine having a melting point of 180–182° C.

(e) With piperidine: 2,4,6,8-tetrapiperidyl-pyrimido-pyrimidine having a melting point of 163–165° C.

(f) With Morpholine: 2,4,6,8-tetramorpholyl-pyrimido-pyrimidine having a melting point of 266–268° C.

(g) With p-chloro-aniline: 2,4,6,8-tetra-(p-chloro-anilino)-pyrimido-pyrimidine having a melting point above 330° C.

(h) With ammonia: 2,4,6,8-tetraamino-pyrimido-pyrimidine; did not melt at a temperature up to 350° C.

(i) With methylamine: 2,4,6,8-tetra-methylamino-pyrimido-pyrimidine having a melting point of 202–204° C.

EXAMPLE 27

2,6-Diamorpholyl-4,8-Dihydroxy-Pyrimido-Pyrimidine

This compound was prepared by reacting 2,6-dichloro-4,8-dihydroxy-pyrimido-pyrimidine with morpholine in the presence of copper powder.

2.3 gm. (0.01 mol) 2,6-dichloro-4,8-dihydroxy pyrimido-pyrimidine were heated to about 200° C. with 17.4 gm. (0.2 mol) morpholine and a spatula-point-full of copper powder in a sealed heavy-walled glass tube for about 2 hours. The reaction mixture was dissolved in 200 cc. of water. The aqueous solution was filtered, and the pyrimido-pyrimidine compound was precipitated in the form of a yellow, amorphous precipitate by adding concentrated hydrochloric acid to the filtrate. Yield: 2.5 gm. corresponding to 75% of the theoretical yield. The compound was reprecipitated three times from hot dilute sodium hydroxide solution, whereby very fine, yellowish, small needles were obtained which did not melt, even at a temperature of 360° C.

EXAMPLE 28

6-Chloro-4,8-Diamino- Pyrimido-Pyrimidine Compounds

These compounds were obtained by reacting 4,6,8-trichloro-pyrimido-pyrimidine with various amines at room temperature and, if required, accompanied by cooling.

(a) 6-chloro-4,8-di-allylamino pyrimido-pyrimidine: 4.6 gm. (0.08 mol) allylamine dissolved in 15 cc. dioxane were added, while stirring, to a solution of 4.8 gm. (about 0.02 mol) 4,6,8-thrichloro-pyrimido-pyrimidine in 50 cc. dry dioxane. The temperature of the mixture increased slightly due to the exothermic reaction. After allowing the mixture to stand for a short period of time, water was added, whereby the crude reaction product precipitated as a yellowish amorphous precipitate which was filtered off on a vacuum filter and dried at room temperature in a vacuum. Yield: 4.8 gm., corresponding to 87% of the theoretical yield. The crude 6-chloro-4,8-di-allylamino-pyrimido-pyrimidine was purified by recrystallizing it twice from ethanol. The resulting fine, colorless needles melted at 114–116° C.

The following 6-chloro-4,8-diamino-pyrimido-pyrimidine compounds were prepared by proceeding in the same manner as described above under (a), but reacting 4,6,8-thrichloro-pyrimido-pyrimidine with various other amines, as indicated:

(b) With methyl-ethanol-amine: 6-chloro-4,8-di-(methyl-ethanol-amino)-pyrimido-pyrimidine having a melting point of 90–92° C.

(c) With diisopropanol-amine: 6-chloro-4,8-bis-(diisopropanol-amino)-pyrimido-pyrimidine having a melting point of 177–179° C.

(d) With methylamine: 6-chloro-4,8-bis-(methylamino)-pyrimido-pyrimidine having a melting point of 227–229° C.

(e) With diethanol-amine: 6-chloro-4,8-bis-(diethanolamino)-pyrimido-pyrimidine having a melting point of 135–136° C.

(f) With p-nitro-aniline: 6-chloro-4,8-bis-(p-nitro-anilino)-pyrimido-pyrimidine which did not melt on heating up to 350° C.

(g) With 3-methoxy-propyl-amine: 6-chloro-4,8-di-(3-methoxy-propylamine)-pyrimido-pyrimidine having a melting point of 98–100° C.

(h) With o-methoxy-aniline: 6-chloro-4,8-di-(o-methoxy-anilino)-pyrimido-pyrimidine having a melting point of 290–292° C.

(i) With dibenzyl-amine: 6-chloro-4,8-bis-(dibenzylamino)-pyrimido-pyrimidine having a melting point of 160–163° C.

(j) With ethylene-imine: 6-chloro-4,8,di-(ethyleneimino)-pyrimido-pyrimidine: this compound assumed a yellowish color at 130° C. and decomposed at about 170° C.

(k) With semicarbazide: 6-chloro-4,8-disemicarbazido-pyrimido-pyrimidine, which did not melt on heating up to 360° C.

EXAMPLE 29

2,4,6,8-Tetraamino-Dihydroxy-Pyrimido-Pyrimidine Compounds

These compounds were obtained by reacting the corresponding 2,6-dichloro-4,8-diamino-pyrimido-pyrimidine compounds with various amines at elevated temperatures, as described hereinafter.

(a) 2,6-bis-(diethanol amino)-4,8-dipiperidyl-pyrimido-pyrimidine: 36.7 gm. (0.1 mol) 2,6-dichloro-4,8-dipiperidyl-pyrimido-pyrimidine having a melting point of 241–242° C. were heated to 200° C. with 100 gm. diethanol amine and the mixture was kept at said temperature for 10 minutes. After cooling, about 500 cc. of water were added to the reaction mixture, whereby the reaction product precipitated out as a viscous mass. After decanting the water, said mass was triturated with a small amount of acetone, whereby a solid-yellow precipitate was formed. Yield: 26.5 gm., corresponding to 52.4% of the theoretical yield. For analytical purposes the compound was recrystallized four times from acetic acid ethyl ester, whereby dark yellow, fine, small needles having a melting point of 162–163° C. were obtained.

The starting material, 2–6-dichloro-4,8-dipiperidyl-pyrimido-pyrimidine, was prepared by reacting 2,4,6,8-tetrachloro-pyrimido-pyrimidine with piperidine at room temperature.

Other 2,4,6,8-tetraamino-pyrimido-pyrimidine compounds were obtained from various 2,6-dichloro-4,8-diamino-pyrimido-pyrimidine compounds by using other amines in place of diethanolaine and proceeding in the same manner as described under (a).

(b) 2,6-bis-(diethanolamino)-4,8-bis-(diethylamino)-pyrimido-pyrimidine having a melting point of 167–168° C. was obtained by reacting 2,6-dichloro-4,8-bis-(diethylamino)-pyrimido-pyrimidine with diethanolamine.

(c) 2,6-bis-(diethanolamino)-4,8-dipyrrolidyl-pyrimido-pyrimidine having a melting point of 186–187° C. was obtained by reacting 2,6-dichloro-4,8-dipyrrolidino-pyrimido-pyrimidine with diethanol amine.

(d) 2,6-bis-(diethanolamino)-4,8-bis-(diallylamino)-pyrimido-pyrimidine having a melting point of 110° C. was obtained by reacting 2,6-dichloro-4,8-bis-(diallylamino)-pyrimido-pyrimidine with diethanolamine.

(e) 2,6-bis-(diethanolamino)-4,8-bis-(dimethylamino)-pyrimido-pyrimidine having a melting point of 182–183° C. is obtained by reacting 2,6-dichloro-4,8-bis-(dimethylamino)-pyrimido-pyrimidine with diethanolamine.

(f) 2,6-bis-(diethanolamino)-4,8-bis-dibutylamino)-pyrimido-pyrimidine having a melting point of 124–126° C. was obtained by reacting 2,6-dichloro-4,8-bis-(dibutylamino)-pyrimido-pyrimidine with diethanolamine.

(g) 2,6-di-(methyl-ethanol-amino)-4,8-di-piperidyl-pyrimido-pyrimidine, which starts to sinter at 114° C. and melts at 122–124° C., was obtained by reacting 2,6-dichloro-4,8-dipiperidyl-pyrimido-pyrimidine with methyl-ethanol-amine.

(h) 2,6-di-(propyl-ethanol-amino)-4,8-dimorpholyl-pyrimido-pyrimidine having a melting point of 138–139° C. was obtained by reacting 2,6-dichloro-4,8-dimorpholyl-pyrimido-pyrimidine with propyl-ethanol-amine.

(i) 2,6-bis-(diisopropanol-amino)-4,8-dipiperidyl-pyrimido-pyrimidine having a melting point of 182–183° C. was obtained by reacting 2,6-dichloro-4,8-piperidyl-pyrimido-pyrimidine having a melting point of 182–183° C. was obtained by reacting 2,6-dichloro-4,8-piperidyl-pyrimido-pyrimidine with diisopropanol-amine.

(j) 2,6-di-(methyl-ethanol-amino)-4,8-di(dodecyl-ethanol-amino)-pyrimido-pyrimidine having a melting point of 88–90° C. was obtained by reacting 2,6-dichloro-4,8-di-(dodecyl-ethanol-amino)-pyrimido-pyrimidine with methyl-ethanol-amine.

(k) 2,6-bis-(diethanolamino)-4,8-dimorpholyl-pyrimido-pyrimidine having a melting point of 202–204° C. was obtained by reacting 2,6-dichloro-4,8-dimorpholyl-pyrimido-pyrimidine with diethanol amine.

EXAMPLE 30

2,4,6,8-Tetraamino-Pyrimido-Pyrimidine Compounds

These compounds were prepared by reacting the corresponding 2,6-dichloro-4,8-diamino-pyrimido-pyrimidine compounds with various amines at elevated temperature under pressure, as described in detail hereinafter.

(a) 2,6-dimorpholyl-4,8-di-(ethyl-ethanol-amino)-pyrimido-pyrimidine: 7.6 gm. (0.02 mol) 2,6-dichloro-4,8-di-(ethyl-ethanol-amino)-pyrimido-pyrimidine were heated with 20 cc. morpholine at 200° C. for one hour in a sealed thick-walled glass tube. The reaction mixture was diluted with 200 cc. Crude 2,6-dimorpholyl-4,8-di-(ethyl-ethanol-amino)-pyrimido-pyrimidine was precipitated in the form of a yellow, amorphous solid. It was filtered off on a vacuum filter, washed, and dried at 110° C. Yield: 8.7 gm., corresponding to 91% of the theoretical yield. For analytical purposes the compound was recrystallized four times from methanol. The resulting light yellow, microcrystalline, small needles were dried at 130° C./0.1 mm. Their melting point was 190–191° C.

In the same manner as described above under (a), but using various other amines, the following new 2,4,6,8-tetraamino-pyrimido-pyrimidine compounds were prepared:

(b) 2,6-dimorpholyl-4,8-di-(propyl-ethanol-amino)-pyrimido-pyrimidine having a melting point of 41–143° C. was obtained by reacting 2,6-dichloro-4,8-di-(propyl-ethanol-amino)-pyrimido-pyrimidine with morpholine.

(d) 2,6-dimorpholyl-4,8-di-(methyl-ethanolamino)-pyrimido-pyrimidine having a melting point of 207–290° C. was obtained by reacting 2,6-dichloro-4,8-di-methyl-ethanol-amino)-pyrimido-pyrimidine with morpholine.

(d) 2,6-dimorpholyl-4,8-bis-(diethanol-amino)-pyrimido-pyrimidine having a melting point of 209–210° C. was obtained by reacting 2,6-dichloro-4,8-bis-(diethanolamino)-pyrimido-pyrimidine with morpholine.

(e) 2,6-dipiperidyl-4,8-bis-(diethanol-amino)-pyrimido-pyrimidine having a melting point of 182–184° C. was obtained by reacting 2,6-dichloro- 4,8-bis-(diethanolamino)-pyrimido-pyrimidine with piperidine.

(f) 2,6-bis-(diethanolamino)-4,8-bis-(diethanolamino)-pyrimido-pyrimidine having a melting point of 18–186° C. was obtained by reacting 2,6-dichloro-4,8-bis-(diethanolamino)-pyrimido-pyrimidine with diethylamine.

(g) 2,6-dimorpholyl-4,8-bis-(dimethylamino)-pyrimido-pyrimidine having a melting point of 92–193° C. was obtained by reacting 2,6-dichloro-4,8-bis-(dimethylamino)-pyrimido-pyrimidine with morpholine.

(h) 2,6-dipiperidyl-4,8-bis-(isoamylamino)-pyrimido-pyrimidine having a melting point of 192–194° C. was obtained by reacting 2,6-dichloro-4,8-bis-(isoamyl-amino)-pyrimido-pyrimidine with piperidine.

(i) 2,6-dipiperidyl-4,8-dipyrrolidyl-pyrimido-pyrimidine having a melting point of 254–256° C. was obtained by reacting 2,6-dichloro-4,8-dipyrrolydyl-pyrimido-pyrimidine with piperidine.

(j) 2,6-dipiperidyl-4,8-di-(benzyl-ethanol-amino)-pyrimido-pyrimidine having a melting point of 161–163° C. was obtained by reacting 2,6-dichloro-4,8-di-(benzyl-ethanol-amino)-pyrimido-pyrimidine with piperidine.

EXAMPLE 31

4,6,8-Triamino-Pyrimido-Pyrimidine Compounds

These compounds were prepared by reacting 4,6,8-trichloro-pyrimido-pyrimidine with various amines at elevated temperatures, if desired at elevated pressures, and in the presence of copper salts as described in detail hereinafter.

(a) 4,6,8-tri-methylamino)-pyrimido-pyrimidine: 4.8 gm. (0.02 mol) 4,6,8-trichloro-pyrimido-pyrimidine were heated to 200° C. for about 2 hours with 50 cc. of an absolute alcohol solution of methylamine (about 0.2 mol) and 0.1 gm. copper sulfate in a sealed thick-walled glass tube. The reaction mixture was diluted with about 300 cc. water, filtered, and concentrated by evaporation to ⅓ of its volume. After allowing the mixture to stand for several hours the crude 4,6,8-tri-(methylamino)-pyrimido-pyrimidine was precipitated in the form of a brown solid similar in texture to cotton. Yield: 4 gm., corresponding to 91% of the theoretical yield. For analytical purposes the compound was recrystallized three times from water and the resulting colorless very fine, wool-like fibers were dried at 130° C./0.1 mm. Melting point: 188–189° C.

The following 4,6,8-triamino-pyrimido-pyrimidine compounds were prepared by following the procedure described above under (a), but using in place of methylamine other amines as indicated.

(b) With ethylamine: 4,6,8-tri-(ethylamino)-pyrimido-pyrimidine; melting point 83–85° C.

(c) With propylamine: 4,6,8-tri-(propyl-amino)-pyrimido-pyrimidine; melting point 84–86° C.

(d) With dimethylamine: 4,6,8-tri-(dimethyl-amino)-pyrimido-pyrimidine; melting point 92–93° C.

(e) With β-hydroxy-ethylamine: 4,6,8-tri-(β-hydroxyethylamino)-pyrimido-pyrimidine; melting point 83–85° C.

(f) With morpholine: 4,6,8-trimorpholyl-pyrimido-pyrimidine; melting point 182–184° C.

(g) With aniline: 4,6,8-trianilino-pyrimido-pyrimidine; melting point 203–204° C.

(h) With p-chloro-aniline: 4,6,8-tri-(p-chloro-anilino)-pyrimido-pyrimidine; melting point 274–275° C.

(i) With o-methoxy-aniline: 4,6,8-tri-(o-methoxy-anilino)-pyrimido-pyrimidine; melting point 214–215° C.

Additional compounds of Formula II may be prepared following similar procedures as above and other procedures, such as described in U.S. Pat. No. 3,031,450 to Fischer and in U.S. Pat. No. 3,322,755 to Roch, which are both incorporated herein by reference.

BIOLOGICAL EFFECTS

These compounds may be assayed for its effect on the human colon carcinoma cell line, HT-29 obtained from ATCC, (Rockville, Md.) to ascertain the degree of growth inhibition. Growth inhibition of this cell line is thought to be indicative of a benefit on precancerous lesions and neoplasms. The cell line and growth assay employed for these experiments is well characterized, and is used by the United States National Cancer Institute in its screening program for new anti-cancer drugs.

Drug stock solutions were made in 100% DMSO then diluted with RPMI media for cell culture testing. All drug solutions were prepared fresh on the day of testing. The cultured cells were obtained at passage #118 and grown in RPMI media supplemented with 5% fetal calf serum, and 2 mM glutamine, 100 U/ml penicillin, 100 U/ml streptomycin, and 0.25 µ/ml amphotericin. The cultures were maintained in a humidified atmosphere of 95% air and 5% $CO_2$ at 37° C. The cultures were passaged at preconfluent densities using a solution of 0.05% trypsin and 0.53 mM EDTA. All experiments involved HT-29 cells between passages 120 and 140. Cells were plated at the following densities to obtain cultures used for the experiments: 500 cells/well for 96 well flat-bottom microtiter plates, $1 \times 10^6$ cells per 25 $cm^2$ flask, or $4 \times 10^6$ cells per 75 $cm^2$ flask.

One method to measure growth inhibition is to measure apoptosis and necrosis by using an assay which allows for the simultaneous measurement of both types of cell death based on morphological characteristics of apoptotic cells (i.e., condensed chromatin) and membrane permeability. Drug preparation and cell culture conditions were the same as above. Confluent cultures were assayed for apoptosis and necrosis by fluorescent microscopy following labeling with acridine orange and ethidium bromide. Floating and attached cells were collected by trypsinization and washed three times in PBS. One ml aliquots of $1 \times 10^6$ cells were centrifuged (300 g). The pellet was resuspended in 25 µl media and 1 µl of a dye mixture containing 100 µg/ml acridine orange and 100 µg/ml ethidium bromide prepared in PBS and mixed gently. Ten µl of mixture was placed on a microscope slide and covered with a 22 $mm^2$ coverslip and examined under 40x dry objectives using epilumination and filter combination.

An observer blinded to the identity of the treatments scored at least 100 cells per sample. Apoptotic cells were identified by nuclear condensation of chromatin stained by the acridine orange or ethidium bromide. Necrotic cells were identified by uniform labeling of the cell with ethidium bromide. These results are provided below.

TABLE 1

Apoptosis Effects for Compounds No. 10 and 29(a)

| Drug Concentration (µM) | | |
|---|---|---|
| Ex. No. 29(a) | Ex. No. 10 | % Apoptotic Cells |
| 0 | 0 | 4 |
| 1 | 0 | 6 |
| 5 | 0 | 8 |
| 10 | 0 | 5 |
| 25 | 0 | 0 |
| 50 | 0 | 54 |
| 0 | 600 | 19 |
| 1 | 600 | 26 |
| 5 | 600 | 81 |
| 10 | 600 | 93 |
| 25 | 600 | 88 |
| 50 | 600 | 95 |

The compounds of Examples 1–31 can be formulated with pharmaceutically acceptable carriers into unit dosage forms in a conventional manner so that the patient in need of therapy for precancerous lesions can periodically (e.g. once or more per day) take a compound according to the method of this invention. It has been found that colonic bacteria will convert the sulfonyl derivatives in part to still unidentified metabolite (s). Specifically, when cis-5-fluoro-2-methyl-1-[p-(methyl-sulfonyl)benzylidene]indene-3-acetic acid prepared according to the procedure of Example 10 is introduced into an anerobic chamber containing an aqueous suspension of human fecal material, and incubated for 1 to 24 hours, the sulfonyl compound is converted to an unknown derivative, as verified by high pressure liquid chromatography.

The exact initial dose of the sulfonyl derivatives used in the method of this invention can be determined with reasonable experimentation, but it is believed to be less than 2 grams per day.

Likewise, the exact initial dose of the pyrimido-pyrimidine derivatives used in the method of this invention can be determined with reasonable experimentation, but it is believed to be less than or equal to that found to be effective for dipyridamole, or mopidamol.

It will be understood that various changes and modifications can be made in the details of procedure, formulation and use without departing from the spirit of the invention, especially as defined in the following claims.

We claim:

1. A method of treating a patient with precancerous lesions, comprising administering to the patient with precancerous lesions sensitive to such treatment a pharmacologically effective amount of a synergistic combination of compound of the Formula I:

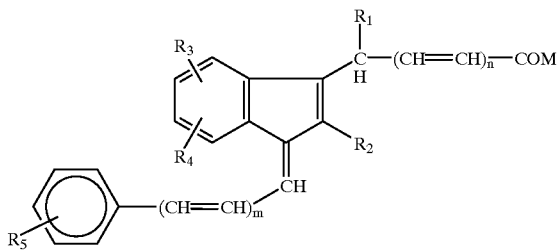

(I)

wherein $R_1$ is selected from the group consisting of hydrogen, lower alkyl, or haloalkyl;

$R_2$ is selected from the group consisting of hydrogen or alkyl;

$R_3$ and $R_4$ are one or more members each independently chosen from the group consisting of hydrogen, alkyl, acyloxy, alkoxy, nitro, amino, acylamino, alkylamino, diakylamino, dialkylaminoalkyl, sulfamyl, alkythio, mercapto, hydroxy, hydroxyalkyl, alkylsulfonyl, halogen, cyano, carboxyl, carbalkoxy, carbarnido, haloalkyl or cycloalkoxy;

$R_5$ is an alkylsulfonyl;

m is 0 or 1;

n is 0 or 1; and

M is selected from the group consisting of hydroxy, substituted lower alkoxy, amino, alkylamino, dialkylamino, N-morpholino, hydroxyalkylamino, polyhydroxyamino, N-morpholino, hydroxyalkylamino, polyhydroxyamino, dialkylaminoalkylarnino, aminoalkylamino, and the group OMe, wherein Me is a cation; and compound of the Formula II:

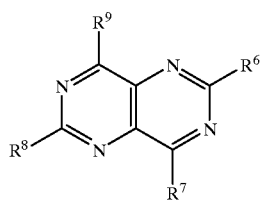

(II)

wherein from two to four, inclusive, of the substituents $R_6$, $R_7$, $R_8$ and $R_9$ are basic moieties selected from the group consisting of amino, lower alkylamino, dialkylamino wherein the alkyl moieties have from 1 to 12 carbon atoms, mono- (hydroxy-lower alkyl) amino, di-(hydroxy-lower alkyl)-amino, (hydroxy-lower alkyl)-alkyl-amino wherein the alkyl moiety has from 1 to 12 carbon atoms, (lower alkoxy-lower alkyl)-amino, lower alkenyl-amino, cyclohexyl-amino, phenyl-amino, halophenyl-amino, nitrophenyl-amino, (lower alkoxy-phenyl)-amino, [(di-lower alkyl-amino)-phenyl]-amino, benzylamino, semicarbazidyl, hydrazinyl, guanidyl, ethyleneimino, piperidyl, lower alkyl-piperidyl, lower alkoxy-piperidyl, hydroxy-piperidyl, pyrrolidyl, lower alkyl-pyrrolidyl, lower alkoxy-pyrrolidyl, hydroxy-pyrrolidyl, morpholyl, lower alkyl-morpholyl, lower alkoxy-morpholyl, hydroxy-morpholyl, tetrahydropyridyl, lower alkyl-tetrahydropyridyl, lower alkoxy-tetrahydropyridyl, hydroxy-tetrahydropyridyl, hexamethyleneimino, lower alkyl-hexamethyleneimino, lower alkoxy-hexamethyleneimino, hydroxy-hexamethyleneimino, tetrahydroquinolyl, lower alkyl-tetrahydroquinolyl, lower alkoxy-tetrahydroquinolyl, hydroxy-tetrahydroquinolyl, piperazyl, lower alkylpiperazyl, lower alkoxy-piperazyl, hydroxy-piperazyl and N'-lower alkyl-piperazyl, and the remaining substituents $R_6$ to $R_9$ are selected from the group consisting of hydrogen, halogen, hydroxyl, mercapto, lower alkyl, phenyl, lower alkoxy, di-lower-alkyl-amino-lower alkoxy and lower alkyl-thio, phenyl-thio, benzyl-thio, lower alkoxy-lower alkoxy, their non-toxic alkali metal salts and their non-toxic acid addition salts.

2. A method according to claim 1 wherein $R_3$ and $R_4$ are selected from alkyl, acyloxy, alkoxy, halogen, haloalkyl or cycloalkoxy.

3. A method according to claim 2 wherein $R_1$ is hydrogen.

4. A method according to claim 1 wherein M is hydroxy or methoxy.

5. A method according to claim 1 wherein $R_6$ and $R_8$ are each diethanolamino.

6. A method according to claim 5 wherein $R_7$ is piperidyl.

7. A method according to claim 6 wherein the compound of Formula I is α-(1-p-methylsulfonylbenzylidene)-2-methyl-5-fluoro-3-indenyl-acetic acid and pharmaceutically acceptable salts thereof, and the compound of Formula II is 2,6-bis-(diethanol amino)-4,8-dipiperidyl-pyrimido-pyrimidine.

8. A method of inhibiting the growth of neoplastic cells, comprising exposing said cells sensitive to the compounds below with an effective amount of a synergistic combination of compound to the Formula I:

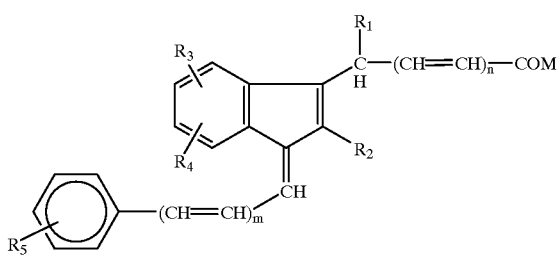

(I)

wherein R₁ is selected from the group consisting of hydrogen, lower alkyl, or haloalkyl;

R₂ is selected from the group consisting of hydrogen or alkyl;

R₃ and R₄ are one or more members each independently chosen from the group consisting of hydrogen, alkyl, acyloxy, alkoxy, nitro, amino, acylamino, alkylamino, diakylamino, dialkylaminoalkyl, sulfamyl, alkythio, mercapto, hydroxy, hydroxyalkyl, alkylsulfonyl, halogen, cyano, carboxyl, carbalkoxy, carbamido, haloalkyl or cycloalkoxy;

R₅ is an alkylsulfonyl;

m is 1 or 1;

n is 0 or 1; and

M is selected from the group consisting of hydroxy, substituted lower alkoxy, amino, alkylamino, dialkylamino, N-morpholino, hydroxyalkylamino, polyhydroxyamino, N-morpholino, hydroxyalkylamino, polyhydroxyamino, dialkylaminoalkylamino, aminoalkylamino, and the group OMe, wherein Me is a cation; and compound of the Formula II:

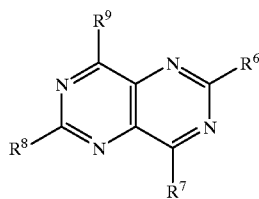

(II)

wherein from two to four, inclusive, of the substituents R₆, R₇, R₈ and R₉ are basic moieties selected from the group consisting of amino, lower alkylamino, dialkylamino wherein the alkyl moieties have from 1 to 12 carbon atoms, mono- (hydroxy-lower alkyl) amino, di-(hydroxy-lower alkyl)-amino, (hydroxy-lower alkyl)-alkyl-amino wherein the alkyl moiety has from 1 to 12 carbon atoms, (lower alkoxy-lower alkyl)-amino, lower alkenyl-amino, cyclohexyl-amino, phenyl-amino, halophenyl-amino, nitrophenyl-amino, (lower alkoxy-phenyl)-amino, [(di-lower alkyl-amino)-phenyl]-amino, benzylamino, semicarbazidyl, hydrazinyl, guanidyl, ethyleneimino, piperidyl, lower alkyl-piperidyl, lower alkoxy-piperidyl, hydroxy-piperidyl, pyrrolidyl, lower alkyl-pyrrolidyl, lower alkoxy-pyrrolidyl, hydroxy-pyrrolidyl, morpholyl, lower alkyl-morpholyl, lower alkoxy-morpholyl, hydroxy-morpholyl, tetrahydropyridyl, lower alkyl-tetrahydropyridyl, lower alkoxy-tetrahydropyridyl, hydroxy-tetrahydropyridyl, hexamethyleneimino, lower alkyl-hexamethyleneimino, lower alkoxy-hexamethyleneimino, hydroxy-hexamethyleneimino, tetrahydroquinolyl, lower alkyl-tetrahydroquinolyl, lower alkoxy-tetrahydroquinolyl, hydroxy-tetrahydroquinolyl, piperazyl, lower alkylpiperazyl, lower alkoxy-piperazyl, hydroxy-piperazyl and N'-lower alkyl-piperazyl, and the remaining substituents R₆ to R₉ are selected from the group consisting of hydrogen, halogen, hydroxyl, mercapto, lower alkyl, phenyl, lower alkoxy, di-lower-alkyl-amino-lower alkoxy and lower alkyl-thio, phenyl-thio, benzyl-thio, lower alkoxy-lower alkoxy, their non-toxic alkali metal salts and their non-toxic acid addition salts.

9. A method according to claim 8 wherein R₃ and R₄ are selected from alkyl, acyloxy, alkoxy, halogen, haloalkyl or cycloalkoxy.

10. A method according to claim 9 wherein R₁ is hydrogen.

11. A method according to claim 8 wherein M is hydroxy or methoxy.

12. A method according to claim 8 wherein R₆ and R₈ are each diethanolamino.

13. A method according to claim 12 wherein R₇ is piperidyl.

14. A method according to claim 13 wherein the compound of Formula I is α-(1-p-methylsulfonylbenzylidene)-2-methyl-5-fluoro-3-indenyl-acetic acid and pharmaceutically acceptable salts thereof, and the compound of Formula II is 2,6-bis-(diethanol amino)4,8-dipiperidyl-pyrimido-pyrimidine.

* * * * *